(12) United States Patent
Vogt et al.

(10) Patent No.: US 11,160,594 B2
(45) Date of Patent: Nov. 2, 2021

(54) BONE CEMENT APPLICATOR WITH A CLOSABLE GAS SUPPLY OPENING

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 189 days.

(21) Appl. No.: 16/239,707

(22) Filed: Jan. 4, 2019

(65) Prior Publication Data

US 2019/0216516 A1 Jul. 18, 2019

(30) Foreign Application Priority Data

Jan. 18, 2018 (DE) ...................... 10 2018 101 041.9

(51) Int. Cl.
*A61B 17/88* (2006.01)
*A61F 2/46* (2006.01)
(Continued)

(52) U.S. Cl.
CPC ...... *A61B 17/8822* (2013.01); *A61B 17/8819* (2013.01); *A61B 17/8827* (2013.01);
(Continued)

(58) Field of Classification Search
CPC ............ A61B 17/8822; A61B 17/8819; A61B 17/8827; A61B 17/8811; A61B 17/8833;
(Continued)

(56) References Cited

U.S. PATENT DOCUMENTS 5,193,907 A 3/1993 Faccioli et al.
5,435,645 A 7/1995 Faccioli et al.
(Continued)

FOREIGN PATENT DOCUMENTS

DE 4030832 4/1992
DE 102009031178 9/2010
(Continued)

OTHER PUBLICATIONS

Charnley et al., "Anchorage of the Femoral Head Prosthesis to the Shaft of the Femur", Journal of Bone and Joint Surgery, 1960, 42, pp. 28-30.
(Continued)

*Primary Examiner* — Kevin T Truong
*Assistant Examiner* — Tracy L Kamikawa
(74) *Attorney, Agent, or Firm* — Stradley Ronon Stevens & Young, LLP

(57) ABSTRACT

A device for producing a bone cement dough from a monomer liquid and a cement powder and dispensing the bone cement dough. The device includes a cartridge holding the cement powder in an internal space. A monomer receptacle screws onto the cartridge, forms a chamber, and has a plunger with a passage that is permeable to gases and the monomer liquid but is impermeable to the cement powder and that connects the internal space to the chamber. The plunger tightly closes the internal space with the exception of the passage. A gas supply opening is arranged in the wall of the monomer receptacle. A monomer liquid container holds the monomer liquid and is located in the chamber. An opening facility opens the container, and closes the gas supply opening before opening the container. Also provided is a method for producing and dispensing the bone cement dough.

18 Claims, 12 Drawing Sheets

(51) Int. Cl.
*B01F 15/00* (2006.01)
*B01F 13/00* (2006.01)

(52) U.S. Cl.
CPC ........ *A61F 2/4601* (2013.01); *B01F 13/0023* (2013.01); *B01F 13/0052* (2013.01); *B01F 15/00071* (2013.01); *B01F 15/00512* (2013.01); *A61B 17/8811* (2013.01); *A61B 17/8833* (2013.01); *A61B 2017/8813* (2013.01); *A61B 2017/8838* (2013.01); *B01F 2215/0029* (2013.01)

(58) Field of Classification Search
CPC ..... A61B 2017/8813; A61B 2017/8838; A61F 2/4601
See application file for complete search history.

(56) References Cited

U.S. PATENT DOCUMENTS

| | | | |
|---|---|---|---|
| 5,588,745 A | 12/1996 | Tanaka et al. | |
| 5,934,803 A * | 8/1999 | Hutter | A61B 17/8827 366/139 |
| 5,997,544 A | 12/1999 | Nies et al. | |
| 6,403,257 B1 * | 6/2002 | Christian | C01G 45/02 423/599 |
| 6,709,149 B1 | 3/2004 | Tepic | |
| 7,073,936 B1 * | 7/2006 | Jonsson | B01F 15/0279 366/139 |
| 7,744,270 B2 * | 6/2010 | Plishka | A61B 17/8827 366/189 |
| 7,938,572 B2 * | 5/2011 | Lidgren | A61B 17/8833 366/108 |
| 9,186,635 B2 * | 11/2015 | Bielenstein | B01F 15/0258 |
| 2002/0118595 A1 * | 8/2002 | Miller | B01F 13/0052 366/130 |
| 2010/0249753 A1 * | 9/2010 | Gaisser | B01F 13/0023 604/519 |
| 2014/0192611 A1 | 7/2014 | Sasaki et al. | |
| 2016/0015854 A1 * | 1/2016 | Vogt | B01F 15/0278 523/116 |
| 2016/0100875 A1 * | 4/2016 | Faccioli | B01F 13/0023 606/94 |
| 2016/0278836 A1 * | 9/2016 | Foster | B01F 7/00666 |
| 2016/0324559 A1 * | 11/2016 | Vogt | B01F 15/0237 |

FOREIGN PATENT DOCUMENTS

| | | |
|---|---|---|
| DE | 102016121606 | 5/2018 |
| EP | 0692229 | 1/1996 |
| EP | 0796653 | 9/1997 |
| EP | 1912597 | 5/2010 |
| EP | 1883379 | 9/2013 |
| EP | 2974681 A1 | 1/2016 |
| JP | H06-261932 | 9/1994 |
| JP | 2013-000335 | 1/2013 |
| WO | 00355506 | 6/2000 |

OTHER PUBLICATIONS

English Translation of the "Notification of Reasons for Refusal" dated Oct. 29, 2019 by the Japanese Patent Office for counterpart Japanese Patent Application No. 2019-006011.

* cited by examiner

BONE CEMENT APPLICATOR WITH A CLOSABLE GAS SUPPLY OPENING

RELATED APPLICATION

This application claims the benefit of priority to German Patent Application Number DE 102018101041.9, filed on Jan. 18, 2018, the contents of which are incorporated in this application by reference.

TECHNICAL FIELD

The invention relates to a device for production of a bone cement dough from a monomer liquid and a cement powder as starting components of the bone cement dough, and for dispensing of the mixed bone cement dough.

The invention also relates to a method for production of a bone cement dough, in particular of a low-viscosity pasty polymethylmethacrylate bone cement dough for augmentation of vertebral bodies.

Specifically, the subject matter of the invention is a device for separate storage of the cement powder and the monomer liquid of polymethylmethacrylate bone cement (PMMA bone cement), for subsequent mixing of the cement powder with the monomer liquid in order to produce a bone cement dough, and for dispensing of the mixed bone cement dough. The low-viscosity bone cement dough produced using the device is intended for the augmentation of fractured vertebral bodies and for the filling of pedicle screws and/or for spondylodesis. Preferably, the device according to the invention is a full-prepacked cementing system.

BACKGROUND OF THE DISCLOSURE

Polymethylmethacrylate (PMMA) bone cements are based on the pioneering work of Sir Charnley. Charnley, J., Anchorage of the femoral head prosthesis of the shaft of the femur, J. Bone Joint Surg. 42, at 28-30 (1960). Conventional PMMA bone cements consist of a liquid monomer component and a powder component. The monomer component generally contains the monomer, methylmethacrylate, and an activator (N,N-dimethyl-p-toluidine) dissolved therein. The powder component, also called cement powder or bone cement powder, comprises one or more polymers that are produced through polymerization, preferably suspension polymerization, based on methylmethacrylate and co-monomers, such as styrene, methylacrylate or similar monomers, a radiopaquer, and the initiator, dibenzoylperoxide. Mixing the powder component and the monomer component, swelling of the polymers of the powder component in the methylmethacrylate generates dough that can be shaped plastically and is the actual bone cement or bone cement dough. During the mixing of powder component and monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the bone cement dough increases until the bone cement dough solidifies.

PMMA bone cements can be mixed by mixing the cement powder and the monomer liquid in suitable mixing beakers with the aid of spatulas.

It is also part of the prior art to fill polymethylmethacrylate bone cement powder and a monomer liquid into cartridge systems during a surgery (OR) and to mix the two starting components through manual actuation of mixing devices, such as axially mobile mixing rods or rotating mixers, and to subsequently extrude the polymethylmethacrylate bone cement dough thus formed from the cartridges.

Cementing systems, in which both the cement powder and the monomer liquid are already packed in separate compartments of the mixing devices and are mixed with each other in the cementing system only right before application of the cement, are a development of cementing technology. Such closed full-prepacked mixing devices have been proposed in EP 0 692 229 A1, DE 10 2009 031 178 B3, U.S. Pat. Nos. 5,997,544 A, 6,709,149 B1, WO 00/35506 A1, EP 0 796 653 A2, and U.S. Pat. No. 5,588,745 A.

Patent DE 10 2009 031 178 B3 discloses a storage and mixing device as a full-prepacked cementing system, in which the starting components required for the production of the bone cement dough are stored already in the storage and mixing device and can be combined and mixed in the storage and mixing device.

WO 00/035506 A1 proposes a device, in which the polymethylmethacrylate cement powder is stored in a cartridge, whereby the cement powder takes up the entire volume of the cartridge and the volume of the intervening spaces between the particles of the cement powder is equal to the volume of the monomer liquid required for the production of bone cement dough using the cement powder stored in the cartridge.

Patents DE 40 30 832 C2 and U.S. Pat. No. 5,435,645 describe a full-prepacked cementing system, in which the monomer liquid is drawn into a powder container of a cartridge containing a cement powder after an ampoule is opened. The mixing of the cement powder and monomer liquid takes place by shaking the cartridge. The ampoule is opened through axial insertion of an externally accessible plunger into the cartridge. The plunger pushes the ampoule against a holder and thus breaks an ampoule head supported in the holder off the ampoule in order to release the monomer liquid from the ampoule.

A similar mixing system is disclosed in patent EP 1 883 379 B1, in which the mixing of the cement components is also effected by shaking the cartridge. The dispensing opening of the cartridge is closed by a membrane.

Patent EP 1 912 597 B1 proposes a mixing system, in which a ring-shaped mixing element that is mobile along a guidance is used to mix cement powder and monomer liquid. The mixing element is arranged coaxial with respect to a guidance in this context. A cylindrical element pushes a supported ampoule containing a monomer liquid against a mandrel and thus fractures the ampoule.

These bone cement mixing systems are complex and therefore have an expensive design. Moreover, the internal space containing the cement powder can be sterilized with a sterilizing gas only in an at least partially disassembled state. Accordingly, an additional installation step is required after sterilization of the content of the devices and this step may possibly counteract the sterilization that has taken place and render the fabrication of the devices more difficult and more laborious.

SUMMARY OF THE INVENTION

Accordingly, it is an object of the present invention to overcome the disadvantages of the prior art. Specifically, it is an object of the invention to develop a device that is intended and well-suited for the mixing of the bone cement dough from the starting components, as well as to develop a method for the production of a bone cement dough, in particular of a low-viscosity pasty polymethylmethacrylate bone cement dough, whereby the bone cement dough is produced from a cement powder and a monomer liquid, by which the drawbacks of the previous devices and methods are overcome.

It is another object of the invention to improve a device of this type appropriately such that the device can be fabricated inexpensively and largely from plastics and such that it is easy to use and is only minimally susceptible to operating errors. One reason for the design to be inexpensive is to allow the device to be used just a single time for hygienic reasons. Moreover, the device should be as easy to use as possible. Moreover, the sterilization of the fully assembled device without monomer vapors of the monomer liquid or the monomer liquid itself possibly being released during the use of the device and/or of the method should be made possible. Accordingly, although the inside of the device is to be accessible to a sterilizing gas, the mixing of the bone cement dough is to take place in a fully closed system without there being a risk of the starting components exiting.

The device and the method shall provide a PMMA bone cement dough that can be used for vertebroplasty and kyphoplasty to be produced and to be applied. The PMMA bone cement doughs are particularly fluid (low-viscosity) as compared to bone cement doughs for the anchoring of prostheses since it must be possible to press them into small intervening spaces of fractured vertebrae and into narrow hollow spaces of pedicle screws. The formation of air bubbles and/or gas bubbles is less critical in a more fluid bone cement dough, as gas bubbles can escape more easily from a low-viscosity bone cement dough.

As many processes as possible or all of the processes taking place in the device, such as the mixing of the starting components, the opening of the monomer liquid container and, if possible, also the dispensing of the bone cement dough, are to take place in the smallest number of working steps and the device is to be easily operated by hand Preferably, no additional apparatus other than the device itself and no electrically or other motor-driven drive is to be required for the use of the device and application of the method. Accordingly, the device and the method should be usable without any problems even under difficult conditions.

In this context, the handling of the device is to be maximally simplified in order to basically prevent operating errors resulting from installation steps taking place incorrectly. It should be feasible for the medical user to actuate the device immediately after removing it from a packaging. Additional installation and working steps are to be omitted due to the design of the device and the method. Preferably, the device is to also ensure the secure storage of cement powder and monomer liquid in separate compartments such that any inadvertent mixing of the cement components during storage of the device is excluded. The device is to allow for sterilization with ethylene oxide gas. For this purpose, the cement powder stored in the device must be accessible to ethylene oxide.

Accordingly, it is another object of the invention to develop a device for storage and mixing of cement powder and monomer liquid, whereby the polymethylmethacrylate bone cement dough produced by mixing the cement components is intended, in particular, for the augmentation of fractured vertebral bodies and for the filling of pedicle screws. Moreover, the device is to allow for extrusion of the polymethylmethacrylate bone cement dough thus produced without a separate extrusion device being required. A full-prepacked cementing system is to be developed, in which the medical user is not exposed or cannot become exposed to the monomer liquid and the cement powder. A closed mixing system is to be provided that is hermetically closed with respect to the surroundings during the mixing process such that no monomer vapors can escape into the surrounding atmosphere. Moreover, the inside of the device is to be accessible to ethylene oxide. In this context, it is important that the cement powder stored in the device and all surfaces present on the inside of the device must be accessible to ethylene oxide. The handling of the device is to be maximally simplified in order to basically prevent operating errors resulting from installation steps taking place incorrectly.

The objects of the invention are met by a device for the production of a bone cement dough from a monomer liquid and a cement powder as starting components of the bone cement dough, and for dispensing of the mixed bone cement dough, the device comprising A) a cartridge with a cylindrical internal space, whereby the cement powder is arranged in the internal space of the cartridge, the cartridge comprises a dispensing opening on a closed front side, the dispensing opening is closed by a removable closure, and whereby the cartridge comprises a thread on a rear side;

B) a monomer receptacle comprising a counter-thread fitting with the thread on the rear side of the cartridge, whereby the monomer receptacle forms a chamber on its inside, the monomer receptacle is screwed using its counter-thread to the thread of the cartridge, the monomer receptacle is mobile, by screw action, in a longitudinal direction with respect to the cartridge, and whereby the monomer receptacle forms a cylindrical plunger on a front side, whereby a passage is provided in the plunger that is permeable to gases and the monomer liquid, but impermeable to the cement powder, whereby the passage connects the internal space of the cartridge to the chamber of the monomer receptacle, whereby the plunger tightly closes the internal space of the cartridge on its rear side except for the passage, and whereby at least one gas supply opening connecting the chamber to the surroundings of the device is arranged in the wall of the monomer receptacle;

C) a monomer liquid container containing the monomer liquid, whereby the monomer liquid container is arranged in the chamber of the monomer receptacle; and D) an opening facility for opening of the monomer liquid container within the chamber of the monomer receptacle, whereby the at least one gas supply opening can be closed by moving the opening facility or by moving a closure that is synchronized to the operation of the opening facility, before the monomer liquid container is opened by the opening facility.

The cylindrical internal space and the cylindrical plunger have a cylindrical geometry with a circular base. By this configuration, the cylindrical plunger can rotate in the cylindrical internal space, when the monomer receptacle carries out a screw motion, and can simultaneously seal the cylindrical internal space on its rear side.

The passage can preferably be formed by multiple channels that are covered by a pore filter that is permeable to the monomer liquid and gases, but is impermeable to the cement powder. Preferably, the passage can be covered additionally by a mesh and/or a sieve by which chips or fragments of the monomer liquid container can be retained.

To seal the plunger with respect to the internal wall of the internal space of the cartridge, at least one circumferential seal on the plunger can be provided, preferably two circumferential seals situated at a distance from each other in the longitudinal direction are provided. The seals can consist of rubber. By this configuration, a negative pressure can be generated in the internal space of the cartridge, when the internal space of the cartridge is increased by unscrewing the monomer receptacle, and the negative pressure can be used to aspirate the monomer liquid from the chamber into the internal space of the cartridge. Moreover, a gas that is present and/or distributed in the bone cement dough can be driven out through the passage and can be driven into the monomer receptacle by the pressure acting on the bone cement dough-gas mixture that is generated by the plunger and/or the monomer receptacle being screwed into the internal space, or can be driven out of the dispensing opening without any bone cement dough escaping from the device outwards between the plunger and the internal wall of the cartridge. This configuration prevents the user or the OR theater from becoming soiled by bone cement dough and prevents unused bone cement dough from being lost.

It is particularly preferred for the invention to provide that the plunger is axially mobile in the internal space of the cartridge such as to be gas-tight.

Likewise, at least one seal, preferably two seals, can be provided on the opening facility by which the at least one gas supply opening of the opening facility can be closed. It is particularly preferred for the invention to provide the at least one gas supply opening to be closable in gas-tight manner, and even more particularly preferably to be closable in pressure-tight manner as well.

The closure is preferred to be a closure stopper that closes the dispensing opening in the closed state in a gas-tight manner. Alternatively, the invention can provide the closure to be permeable to gases, but impermeable to the cement powder and the bone cement dough, whereby this variant is less preferred, since it renders a transfer of the monomer liquid by a negative pressure in the internal space of the cartridge unfeasible.

Due to the at least one gas supply opening, even the inside of the device and, in particular, the cement powder in the internal space of the cartridge can be sterilized through the aid of a sterilizing gas, such as, for example, ethylene oxide. Since the at least one gas supply opening can be closed, the monomer liquid can be prevented from exiting from the monomer receptacle towards the outside. If the at least one gas supply opening can be closed in a gas-tight manner and, preferably, in a pressure-tight manner as well, a negative pressure that can be used to aspirate gases from the bone cement dough can be generated in the chamber of the monomer receptacle or an overpressure can be generated by which the monomer liquid can be transferred and/or aspirated from the chamber into the internal space of the cartridge.

Devices according to the invention can be provided appropriately such that the opening facility comprises a securing facility that prevents the at least one gas supply opening from being opened again after the opening has been closed, whereby the opening facility preferably is connected via a thread to the monomer receptacle and the at least one gas supply opening can be closed when the opening facility is being screwed into the chamber, whereby the securing facility is a reverse motion lock.

This configuration can prevent the at least one gas supply opening from inadvertently being re-opened and monomer liquid from exiting from the device after the monomer liquid container has been opened.

Moreover, the invention can provide a first releasable securing element that prevents the opening facility from being operated and/or a second releasable securing element that prevents the monomer receptacle from being screwed into the cartridge.

This ensures that the device is not activated and/or operated inadvertently during transport or while the device is being provided.

Moreover, the invention can provide a mandrel or a cutting edge for fracturing the monomer liquid container to be arranged on the side of the plunger facing into the chamber of the monomer receptacle, whereby, preferably, a compressible supporting element, in particular a spring or a foam or an elastic hollow body, is arranged between the plunger and the monomer liquid container, whereby the supporting element keeps the monomer liquid container at a distance from the mandrel or cutting edge.

By this configuration, the monomer liquid container can be opened by the mandrel or the cutting edge at a defined site in the area of the passage such that the monomer liquid can directly flow from the monomer liquid container, which is being opened in this area, through the passage into the internal space of the cartridge. Due to the presence of the supporting element, the monomer liquid container can be prevented from being opened inadvertently during transport, for example by shocks.

Moreover, the invention can preferably provide at least one loose mixing element, in particular at least one loose bead, to be arranged such as to be freely mobile in the internal space of the cartridge.

By this feature, the content of the internal space of the cartridge and/or the cement powder and the introduced monomer liquid can be mixed more efficiently by shaking the cartridge, whereby the at least one mixing element, which is moving or flying back and forth or is being hurled in the internal space of the cartridge, supports the mixing process.

In this context, the invention can provide at least one protrusion to be adjacent to the dispensing opening and/or at least one fin that runs to the dispensing opening and extends into the internal space of the cartridge to be arranged on the front side of the cartridge facing the internal space of the cartridge.

By this design, the at least one mixing element, in particular the at least one bead, can be prevented from becoming positioned in front of the dispensing opening and closing the dispensing opening. The at least one fin preferably extends radially into the internal space of the cartridge, emanating from the side wall of the cartridge to the dispensing opening that is situated on the cylinder axis of the cylindrical internal space. It is particularly preferred for the height of the at least one fin to increase in the direction of the dispensing opening.

Referring to devices according to the invention having at least one mixing element, the invention can provide a deformable receiving element to be arranged, in particular a deformable annular disk to be arranged, on its front side in the internal space of the cartridge, whereby the height of the deformable receiving element preferably increases in a radial direction outward towards the side wall of the internal space.

The at least one mixing element can be pushed into the deformable receiving element by the plunger being screwed into the internal space of the cartridge, whereby the receiving element deforms in the process. By this configuration, the receiving element can receive the at least one mixing element. At the same time, the deformable receiving element is not deformed in the other places such that less unused volume remains in the internal space of the cartridge, in which bone cement dough may remain. By this configuration, a larger fraction of the mixed bone cement dough can be extruded from the internal space of the cartridge and can be utilized.

The receiving element can be made from an elastic material, whereby a hollow body with elastic walls, in particular one made of a rubber, is preferred. Alternatively, the receiving element can just as well be made from a closed-pore material, such as a closed-pore foam. The closed pores prevent any ingress of cement powder and adsorption of monomer liquid on large areas of the accessible surface of the material of the receiving element.

According to the invention, it is preferred to have the receiving element be attached to a cartridge lid so that the front end of the cartridge, and therefore the internal space of the cartridge, can be closed in gas-tight manner on its front side.

Moreover, the invention can provide the at least one loose mixing element with a higher density than polymethylmethacrylate (PMMA), preferably with a density that is twice as high or three times as high as the density of polymethylmethacrylate, whereby the at least one mixing element preferably consists of a corundum, of α-corundum, of a zirconium oxide, of tetragonal $ZrO_2$ or of $ZrO_2$ that is cubic-stabilized with $Y_2O_3$.

Due to the density being higher, the at least one mixing element can be moved well with respect to the bone cement dough when shaken.

The invention can provide a pore filter to be arranged on the passage that is permeable to gases and the monomer liquid, but is impermeable to the cement powder and the bone cement dough.

This arrangement easily prevents the cement powder from penetrating into the chamber of the monomer receptacle and preferably also from penetrating into the passage and from prematurely reacting in this place with the monomer liquid and the passage from being closed by swelling bone cement dough.

The invention can just as well provide the monomer liquid container to be an ampoule made of glass or plastics, and can provide shatter protection, a mesh or a sieve between the passage and the chamber of the monomer receptacle in order to retain any splinters or fragments of the ampoule. By this design the splinters or fragments can be prevented from closing the passage and from inadvertently penetrating into the internal space of the cartridge.

According to a preferred refinement, the present invention can provide the monomer liquid container to be an ampoule made of glass or plastics, whereby the ampoule comprises an ampoule body with a cylindrical wall, and whereby the opening facility comprises a hollow cylinder that is mobile in the monomer receptacle, in a longitudinal direction of the cylindrical chamber of the monomer receptacle, and the hollow cylinder to be flush with the cylindrical wall of the ampoule such that the ampoule can be pushed in the direction of the internal space of the cartridge by the hollow cylinder.

By this configuration, the ampoule, as the monomer liquid container, can be pushed in the direction of the cartridge without the ampoule being fractured by the hollow cylinder on the side facing away from the cartridge. By this orientation, it can be ensured that the ampoule will be fractured on the side facing the internal space of the cartridge.

The hollow cylinder can have perforations or slits in the longitudinal direction. According to the invention, however, it is preferred for the hollow cylinder to be continuous, at least on the front side facing the ampoule, such that no pressure peaks, which may lead to inadvertent fracturing of the wall of the ampoule body, occur on the wall of the ampoule body when the hollow cylinder is being pushed inwards.

As an alternative to an ampoule, the monomer liquid container can just as well be implemented by a film bag that is being torn open, punctured open or cut open in the chamber of the monomer receptacle having the opening facility in order to release the monomer liquid into the chamber of the monomer receptacle.

If the ampoule consists of a plastic material, it must consist of a plastic material that is chemically stable with respect to the monomer liquid. The preferred material for the ampoule is glass.

Referring to devices according to the invention having ampoules with a cylindrical body, the invention can provide that the at least one gas supply opening merges next to the hollow cylinder into the chamber of the monomer receptacle such that, upon a motion of the hollow cylinder into the chamber, the at least one gas supply opening is closed in liquid-tight or gas-tight manner by a side wall of the hollow cylinder, whereby the hollow cylinder preferably comprises at least one circumferential sealing ring for this purpose, particularly preferably comprises two circumferential sealing rings, which travel over the at least one gas supply opening when the hollow cylinder is being moved into the chamber and seal the chamber. Preferably, the at least one gas supply opening is closed in a gas-tight manner by a side wall of the hollow cylinder.

By this configuration, a relatively simple design can be used to make sure that the at least one gas supply opening is being closed and that no monomer liquid can exit afterwards. Preferably, a negative pressure can be generated through a motion of the monomer receptacle into the internal space of the cartridge, when the gas supply opening is being closed in a gas-tight manner.

Moreover, the invention can provide the front side of the plunger limiting the internal space and/or the surface limiting the front side of the internal space to progressively extend in a radial direction into the internal space of the cartridge such that a front base surface and/or a rear base surface of the internal space comprises no edge or no edge with an angle of less than 60°, whereby the front base surface and/or the rear base surface of the internal space preferably have/has a rounded shape.

This configuration prevents a powder in a pointed edge of the internal space from being inaccessible or poorly accessible to the monomer liquid and from not becoming mixed with the monomer liquid and prevents the consistency of the bone cement dough from therefore becoming inhomogeneous or failing to attain the desired mixing ratio.

For the same purpose, the invention can provide the front side of the plunger limiting the internal space and/or the surface limiting the front side of the internal space to have a rounded shape with flanks that rise in the direction of the side walls of the cylindrical internal space (the cylinder jacket surfaces).

In order to attain complete mixing of the bone cement dough, the invention can provide at least one bead to be arranged as a mixing element in the internal space of the cartridge such as to be freely mobile and the radius of the at least one bead to be equal to or smaller than the radius of curvature of the front base surface and/or of the rear base surface of the internal space of the cartridge.

Due to the radius of curvature of the at least one bead, as the mixing element, being adapted to the radius of curvature of the base surfaces, the at least one bead that is being hurled around in the internal space of the cartridge can reach every area of the internal space of the cartridge such that no unmixed or poorly mixed areas that cannot be reached by the at least one bead remain in the internal space of the cartridge.

The invention can just as well provide the opening facility to be connected to the monomer receptacle by a thread and a counter-thread such that the opening facility can be screwed into the chamber of the monomer receptacle and the monomer liquid container can be fractured, cut or punctured by screwing the opening facility into the chamber of the monomer receptacle.

By this configuration, the monomer liquid container can be opened easily in the monomer receptacle.

In this context, the invention can provide the counter-thread of the monomer receptacle to fit both the thread of the cartridge and a thread of the opening facility. The monomer receptacle can then be designed to have a uniform thread, particularly preferably to have a continuous external thread.

Moreover, the invention can provide the thread on the rear side of the cartridge to be an internal thread and the counter-thread of the monomer receptacle to be an external thread that is provided on the lateral external surfaces.

By this configuration, the device can be designed to be particularly compact.

In this context, the invention can provide the plunger to have a larger diameter than the internal thread on the rear side of the cartridge.

By this configuration, the plunger can seal the rear side of the cartridge with respect to the internal wall of the cartridge and can expel the bone cement dough from the internal space of the cartridge over the entire width thereof. Moreover, it is thus not possible to fully unscrew the monomer receptacle from the cartridge. The rear side of the plunger and the beginning of the internal thread of the cartridge jointly form a limit stop beyond which the monomer receptacle cannot be unscrewed from the cartridge such that inadvertent opening of the internal space of the cartridge is precluded.

Moreover, the invention can provide the front side of the cartridge to be closed by a cartridge lid, whereby the dispensing opening is arranged in the cartridge lid and the cartridge lid is connected to the side walls of the cartridge in a gas-tight and liquid-tight manner, whereby the cartridge lid is preferably screwed onto an external thread on the front side of the cartridge.

This configuration simplifies the installation of the device. Accordingly, the monomer receptacle can be inserted into the cartridge from the front and can be screwed into an internal thread as the thread on the rear side of the cartridge even if the plunger has a larger radius than the internal thread (the counter-thread) on the monomer receptacle. Subsequently, the cement powder can be filled in and the internal space of the cartridge is closed on the front side by the cartridge lid.

According to a refinement, the present invention can provide the opening facility to comprise a closure cap that can be screwed onto the rear side of the monomer receptacle and close the chamber on the rear side in a gas-tight manner Preferably, a limit stop preventing the closure cap from being screwed further onto the monomer receptacle is provided.

By this configuration, both the opening facility and the monomer receptacle can be operated through a screw action. Moreover, a gas can be pressed from the internal space of the cartridge into the chamber without the gas being able to exit.

In this context, the invention can provide a sleeve to be arranged on the closure cap that can be plugged or screwed appropriately into the inside of the chamber such that it closes the chamber on its rear side in a gas-tight manner.

The projecting sleeve can be used to open the monomer liquid container.

According to the invention, the sleeve can preferably also be used to close the at least one gas supply opening in the wall of the monomer receptacle in a gas-tight manner. For this purpose, the sleeve particularly preferably comprises at least one circumferential seal, even more particularly preferably two circumferential seals. Accordingly, the invention can permit the sleeve to be shifted in the chamber in a gas-tight manner.

If the closure cap comprises an internal thread that can be screwed onto an external thread on the rear side of the monomer receptacle, the rear wall of the closure cap facing the chamber and the rear end of the wall of the monomer receptacle jointly form the limit stop. In this context, the invention can preferably give the internal thread of the cap a smaller height in the longitudinal direction than the sleeve.

It is particularly preferred for the sleeve to project so far into the chamber that a monomer liquid container arranged in the chamber can be fractured, cut or torn open by the sleeve in the chamber, when the closure cap is screwed onto the monomer receptacle all the way to the limit stop or when the closure cap is being screwed onto the monomer receptacle. If the monomer liquid container is an ampoule made of glass or a plastic material and if the sleeve pushes onto the side walls of the ampoule body, the distance between the front edge of the sleeve and the end of the plunger facing the chamber or the tip of a mandrel arranged on it or a cutting edge arranged on it, with the closure cap being screwed all the way to the limit stop, must be smaller than the height of the ampoule body.

Moreover, in a state of the device in which the monomer receptacle is maximally unscrewed from the internal space of the cartridge up to a limit stop, the invention can provide for a free volume to be present over the cement powder in the thus maximally enlarged internal space of the cartridge, whereby the volume is at least equal to the volume of the monomer liquid in the monomer liquid container, preferably is at least twice as large as the volume of the monomer liquid in the monomer liquid container.

This configuration ensures that a sufficiently large free space is contained in the internal space of the cartridge after the monomer liquid is filled into it such that the content can be mixed well by shaking. If mixing elements are present, the air and/or the gas guarantees the sufficient mobility of the mixing elements in the internal space of the cartridge such that the starting components of the bone cement dough can be mixed well by these mixing elements. During the transfer of the monomer liquid into the internal space of the cartridge, the monomer liquid flows into the intervening spaces between the powder particles of the cement powder. If the at least one gas supply opening is closed in a gas-tight manner, the pressure in the internal space of the cartridge is reduced in the process, i.e., no additional gas that was not already present in the internal space of the cartridge and in the chamber is introduced into the internal space of the cartridge. By this configuration, the amount of gas in the mixture is not being increased such that less gas needs to escape from the mixed bone cement dough later on.

The objects on which the present invention is based are also met by a method for the production of a bone cement dough, in particular of a low viscosity polymethylmethacrylate bone cement dough for augmentation of vertebral bodies, whereby the bone cement dough is produced from a cement powder and a monomer liquid and the method is implemented with a device for production of a bone cement dough and for dispensation of the mixed bone cement dough, characterized by the following steps:

A) operating an opening facility of the device, whereby the operation of the opening facility closes, in gas-tight manner, at least one gas supply opening in a wall of a monomer receptacle of the device that connects the surroundings of the device to a chamber on the inside of the monomer receptacle in a gas-permeable manner, and subsequently a monomer liquid container containing the monomer liquid is opened within the chamber of the monomer receptacle;

B) transferring the monomer liquid from the monomer receptacle through a passage that is permeable to gases and the monomer liquid, but is impermeable to the cement powder, and is arranged in a plunger provided on the front side of the monomer receptacle, into an internal space of a cartridge that contains the cement powder;

C) mixing the monomer liquid and the cement powder in the internal space of the cartridge to produce a bone cement dough;

D) pushing out gas that is distributed in the bone cement dough from the internal space of the cartridge by screwing in the monomer receptacle with the plunger on the front side of the monomer receptacle from the rear side of the internal space of the cartridge into the cartridge; and E) extruding the ready-mixed bone cement dough from the internal space of the cartridge through a dispensing opening of the cartridge opposite from the plunger by screwing the monomer receptacle further into the cartridge.

According to the invention, it is preferred that the transfer of the monomer liquid in step B) into the cartridge take place by flowing out, aspirating out, pushing out or a combination of multiple or all of these actions from the chamber of the monomer receptacle into the internal space of the cartridge.

The gas in step D) can be pushed out from the internal space of the cartridge through the passage into the chamber of the monomer receptacle or can be pushed out through the previously opened dispensing opening.

The dispensing opening opposite from the plunger can be opened right before step D) or right before step E).

In methods according to the invention, the invention can provide the method to be implemented with a device according to the invention.

The method then comprises the advantages that can be attained with the device according to the invention.

Moreover, the invention can provide the monomer liquid and the cement powder in step C) to be mixed by shaking the cartridge, whereby the internal space of the cartridge contains, in addition to the cement powder and the monomer liquid, a gas and at least one loose mixing element that is freely mobile in the internal space of the cartridge, in particular at least one loose bead, whereby the at least one mixing element is hurled around in the internal space of the cartridge due to the shaking and the cement powder and the monomer liquid are mixed in that way.

By this method, the cement powder and the monomer liquid can be mixed without any need to use an externally operated mixer such as, for example, a mixing paddle that is moved by a rod that would need to be guided through a sealed feed-through in the cartridge wall.

The invention can allow the monomer liquid container to be opened in step A) by operation of the opening facility, whereby the at least one gas supply opening connecting the chamber to the surroundings of the device in a gas-permeable manner is closed during the operation of the opening facility.

Moreover, the invention can permit the opening facility to be screwed into the monomer receptacle, and the monomer liquid container to be opened by the motion of the opening facility, and the at least one gas supply opening arranged in a wall of the monomer receptacle to be closed beforehand.

By this method, the chamber and the internal space of the cartridge can be sterilized beforehand through the gas supply opening with the aid of a sterilizing gas, whereby the chamber is closed when the monomer liquid container is opened such that no monomer liquid can exit from the chamber.

Preferably, the invention can just as well provide for the monomer liquid container to be an ampoule made of glass or a plastic material and the ampoule to be pushed onto a mandrel or a cutting edge on the side of the plunger facing into the chamber of the monomer receptacle when the ampoule is being opened in step A), such that the ampoule is fractured on this side and the monomer liquid exits from the opened ampoule in the area of the passage.

By this method, the ampoule can be opened at a defined site in the area of the passage by the mandrel or the cutting edge such that the monomer liquid can directly flow from the ampoule, which is being opened in this area, through the passage into the internal space of the cartridge.

According to a refinement of the method according to the invention, the invention can retain the monomer receptacle above the cartridge during step B), preferably during steps A) and B), such that the monomer liquid is driven by the action of gravity when it flows from the chamber through the passage into the internal space of the cartridge.

This refinement allows a separate component for transferring the monomer liquid into the internal space of the cartridge to be omitted. Preferably, in addition, a negative pressure is generated in the internal space of the cartridge by unscrewing the monomer receptacle from the cartridge, and the negative pressure additionally aspirates the monomer liquid from the chamber into the internal space of the cartridge.

Moreover, the invention can precede step A) by a step in which a first securing element preventing an operation of the opening facility is released and/or a second securing element preventing the monomer receptacle from being screwed into the cartridge is released.

This step ensures that the monomer liquid container is not opened inadvertently during transport or the provision of the entire device and that the device is not activated and/or operated inadvertently.

The invention can also allow the monomer receptacle to be unscrewed from the internal space of the cartridge in order to transfer the monomer liquid from the chamber into the internal space of the cartridge in step B), such that the internal space of the cartridge increases and a negative pressure arises in the internal space of the cartridge by which the monomer liquid is aspirated from the chamber into the internal space of the cartridge.

By this method, the transfer of the monomer liquid from the chamber into the internal space of the cartridge can be attained or at least accelerated.

The invention is based on finding, surprisingly, that the inside of the device can be designed with at least one gas supply opening such as to be accessible to a sterilizing gas, whereby, concurrently, an opening facility, which is used to open a monomer liquid container within the device, closes the at least one gas supply opening either by itself or with a separate closure mechanism before the monomer liquid container is opened and the monomer liquid is released within the device, such that the monomer liquid cannot be released from the device when the device is in use. Moreover, using a passage between the chamber of the monomer receptacle and the internal space of the cartridge that is impermeable to the cement powder, but is permeable to the monomer liquid and gases, the cement powder, which is stored in a loose state in the internal space of the cartridge, can be prevented from exiting from the device. These two measures create a device whose inside can be sterilized with a sterilizing gas, such as ethylene oxide, and simultaneously, the starting components cannot exit from the device. Moreover, when the at least one gas supply opening is being closed in gas-tight manner, a negative pressure can be generated on the inside of the device by which the monomer liquid can be aspirated into the internal space of the cartridge and which provides a larger free volume when the starting components are being mixed, such that a better mixing result can be attained through shaking of the device without the amount of gas in the internal space of the cartridge having to be increased, which would have to be extruded from the internal space of the cartridge before the bone cement dough is used.

An exemplary device according to the invention can be assembled from the following components:

a) a hollow cylinder-shaped cartridge, whereby a securing mechanism for a cartridge lid is arranged on a front end of the cartridge, and whereby an internal thread is arranged on the internal wall of the cartridge on the opposite rear-side end of the cartridge;

b) a cartridge lid to be connected by the securing mechanism to the front end of the cartridge in a gas-tight and liquid-tight manner, whereby the cartridge lid has at least one dispensing opening;

c) a closure stopper that is arranged in the dispensing opening of the cartridge lid in a gas-tight and releasable manner;

d) a plunger-shaped, hollow cylinder-shaped monomer receptacle that forms a plunger on a front side, whereby the monomer receptacle comprises at least one screw thread on its jacket surface;

e) a gas- and liquid-permeable, but powder-impermeable passage in an otherwise closed front base surface of the monomer receptacle that connects a chamber on the inside of the monomer receptacle to an internal space of the cartridge;

f) a mandrel that is arranged on the rear side of the closed front base surface of the monomer receptacle;

g) a monomer liquid container containing the monomer liquid whose bottom side is arranged at a distance above the mandrel in the chamber of the monomer receptacle;

h) a sleeve (or hollow cylinder) that can shift and is arranged behind the rear side of the monomer liquid container in the hollow cylinder-shaped monomer receptacle such as to be axially shifted in an appropriate way, such that the sleeve projects beyond the edge of the hollow cylinder-shaped monomer receptacle;

i) a hollow closure cap of the hollow cylinder-shaped monomer receptacle that is closed on one side, whereby an internal thread and a limit stop for the hollow cylinder-shaped monomer receptacle are arranged in the hollow closure cap, whereby the distance between the lower external edge of the closure cap and the limit stop is smaller than the distance between the external end of the sleeve and the edge of the narrow side of the monomer receptacle from which the sleeve projects;

j) at least one ventilation opening in the jacket surface of the hollow cylinder-shaped monomer receptacle that can be closed in a gas-tight manner by shifting the sleeve axially; and k) cement powder that is arranged in the internal space of the cartridge that is bordered by the internal wall of the cartridge, the cartridge lid, and the closed front base surface of the monomer receptacle;

l) whereby the hollow cylinder-shaped monomer receptacle is screwed to the internal thread of the cartridge by its external thread.

The sleeve with the closure cap forms the opening facility for opening the monomer liquid container in the chamber of the monomer receptacle.

The working principle of the exemplary device according to the invention is that, in a sterilization state and/or in the storage state, the plunger-shaped monomer receptacle is screwed appropriately into the cartridge by the at least one external thread such that the plunger touches the cement powder and/or is situated just above it. The cartridge lid of the cartridge is connected to the cartridge in a gas-tight manner. The closure stopper is inserted and/or plugged into the dispensing opening of the cartridge lid in gas-tight manner. The sleeve is appropriately arranged behind the monomer liquid container and thereby above the monomer liquid container such that the at least one gas supply opening for gases is passable and exposed. The sleeve projects beyond the monomer receptacle and is surrounded by the closure cap that is screwed onto the external thread of the monomer receptacle. For activation of the device, the closure cap is rotated downward in the direction of the cartridge lid. In the process, the closure cap pushes the sleeve in the direction of the cartridge lid into the chamber of the monomer receptacle. The at least one ventilation opening is covered by the lid and is thus closed in the process. The sleeve is moved further in the direction of the cartridge head by the closure cap and pushes the monomer liquid container against the mandrel. This step opens the monomer liquid container and the monomer liquid flows out in downward direction. This result is the reason why the device is held with the cartridge downwards during its use. Due to the action of gravity, the monomer liquid starts to flow downward in the direction of the cement powder. The plunger-shaped monomer receptacle is then immediately screwed into the rear side of the cartridge, which is opposite from the cartridge lid. A negative pressure arises in the internal space of the cartridge containing the cement powder. By this negative pressure, the monomer liquid is aspirated into the internal space of the cartridge toward the cement powder. Subsequently, the cartridge containing the starting components is shaken in the internal space of the cartridge. It is advantageous to have freely mobile mixing elements support the mixing process. The bone cement dough is produced by mixing the cement powder with the monomer liquid. Subsequently, the closure stopper is removed from the cartridge lid and the bone cement dough thus produced is extruded by screwing the monomer receptacle in the direction of the cartridge lid. Beforehand, the same motion of the monomer receptacle and/or of the plunger formed on the front side of the monomer receptacle can be used to extrude gas from the bone cement dough.

The diameter of the hollow cylinder-shaped monomer receptacle on its cylinder-shaped front head side is equal to or smaller than the internal diameter of the hollow cylinder-shaped cartridge, and the hollow cylinder-shaped monomer receptacle can be moved axially by its head side in a gas-tight manner.

The invention can provide the external thread of the monomer receptacle with a smaller diameter than the plunger formed on the front side.

Preferably, the sleeve is designed as a hollow cylinder, whereby the front side of the sleeve rests on the monomer liquid container, and whereby the sleeve is closed by a gas-tight separating wall on the inside of the hollow space or on the end of the sleeve. It is important to the working principle of the device that the sleeve can be shifted axially in a gas-tight manner in the hollow cylinder-shaped chamber of the monomer receptacle.

The internal surface of the closure cap and the surface of the front base surface of the monomer receptacle (of the plunger) facing in the direction of the cartridge lid are preferred to be concavely curved.

It is advantageous to have one or more freely mobile mixing bodies arranged in the internal space of the cartridge, whereby spherical mixing bodies are preferred and whereby ceramic spherical mixing bodies are particularly preferred.

Preferably, fins running towards the dispensing opening are arranged on the inside of the cartridge lid.

An exemplary method according to the invention for the mixing and application of polymethylmethacrylate bone cement using the exemplary device according to the invention can be characterized by the following steps proceeding in the order given:

a) positioning the cartridge vertically with the cartridge lid downwards;

b) screwing the closure cap, which is screwed to the hollow cylinder-shaped monomer receptacle, in the direction of the cartridge lid;

c) shifting the sleeve in the direction of the cartridge lid by screwing in the closure cap;

d) closing the at least one gas supply opening in the hollow cylinder-shaped monomer receptacle by using the sleeve;

e) shifting the monomer liquid container in the direction of the mandrel by shifting the sleeve axially;

f) destroying the bottom of the monomer liquid container by the mandrel;

g) monomer liquid flowing out into the chamber of the hollow cylinder-shaped monomer receptacle;

h) unscrewing the monomer receptacle away from the cartridge lid and thereby generating a negative pressure in the internal space of the cartridge;

i) monomer liquid flowing and being aspirated through the passage in the front base surface of the monomer receptacle into the internal space of the cartridge to the polymethylmethacrylate cement powder that is arranged there;

j) manual shaking of the cartridge and thereby mixing of the monomer liquid with the cement powder;

k) forming the bone cement dough from the monomer liquid mixed with the polymethylmethacrylate cement powder;

l) removing the closure stopper from the dispensing opening;

m) screwing the monomer receptacle in the direction of the cartridge lid; and n) extruding the polymethylmethacrylate bone cement from the opened dispensing opening by moving the plunger of the monomer receptacle in the direction of the cartridge lid.

It is to be understood that both the foregoing general description and the following detailed description are exemplary, but are not restrictive, of the disclosure.

BRIEF DESCRIPTION OF THE DRAWING

The disclosure is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE DISCLOSURE

Figure 1:
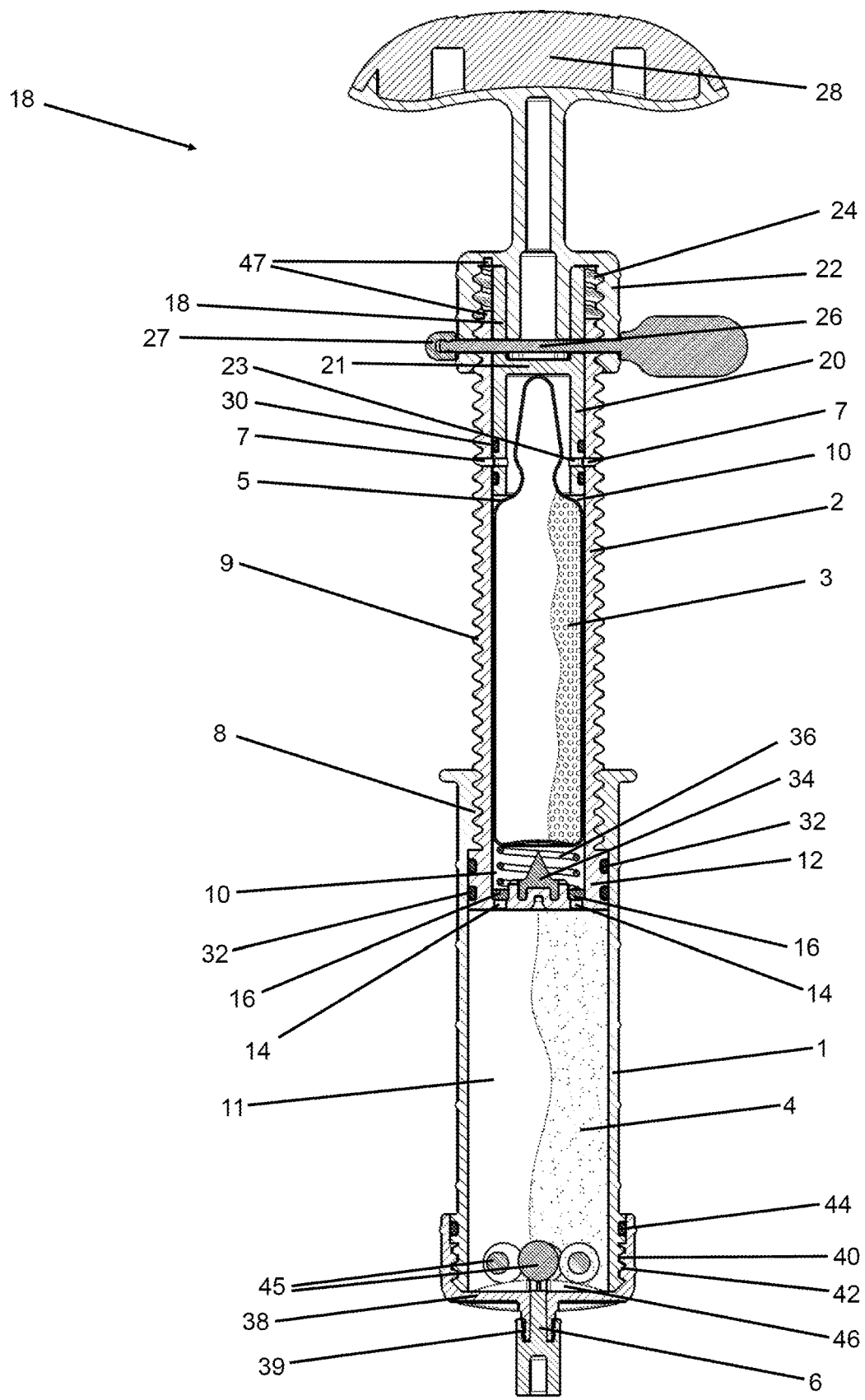
FIG. 1 shows a schematic cross-sectional view of an exemplary first device according to an embodiment of the invention for the production of a bone cement dough.
Figure 2:
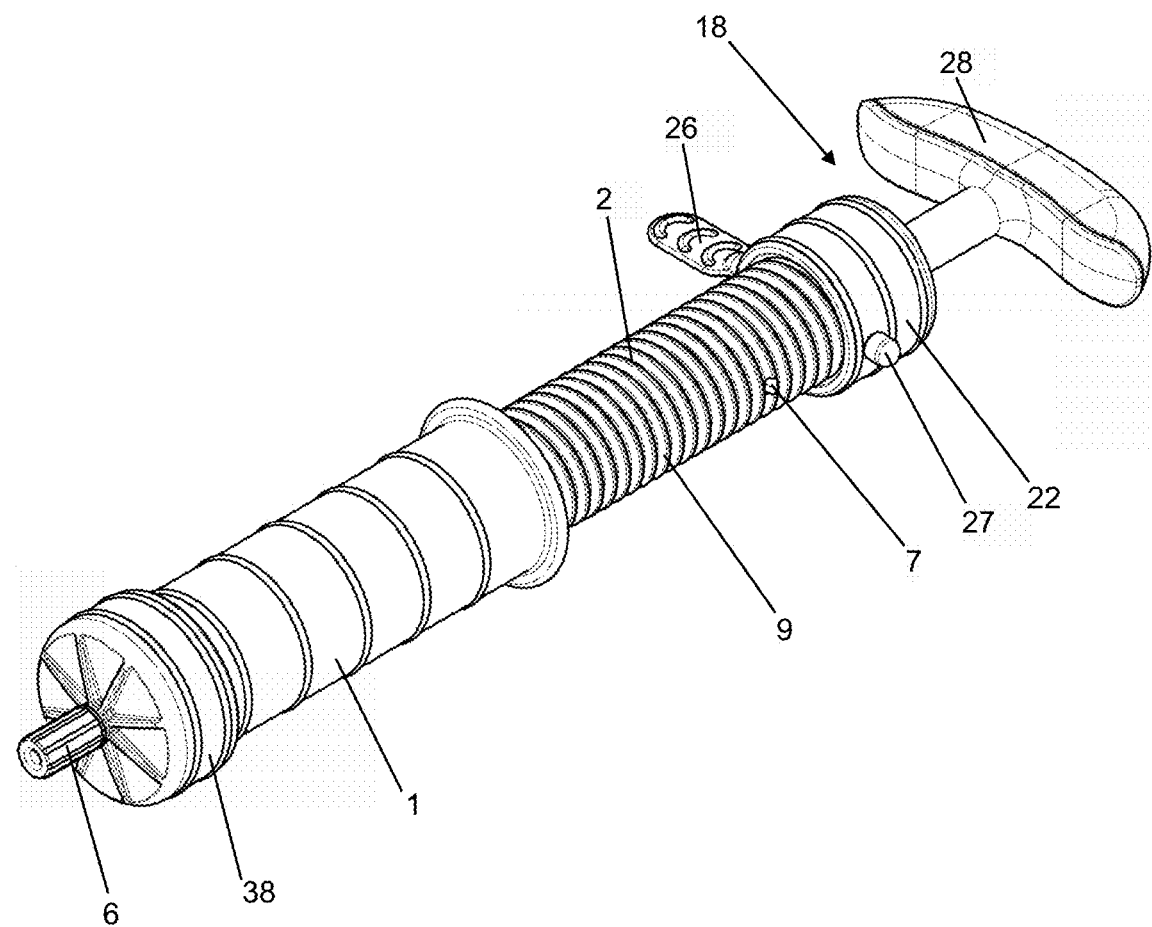
FIG. 2 shows a schematic perspective external view of the first device shown in FIG. 1.
Figure 3:
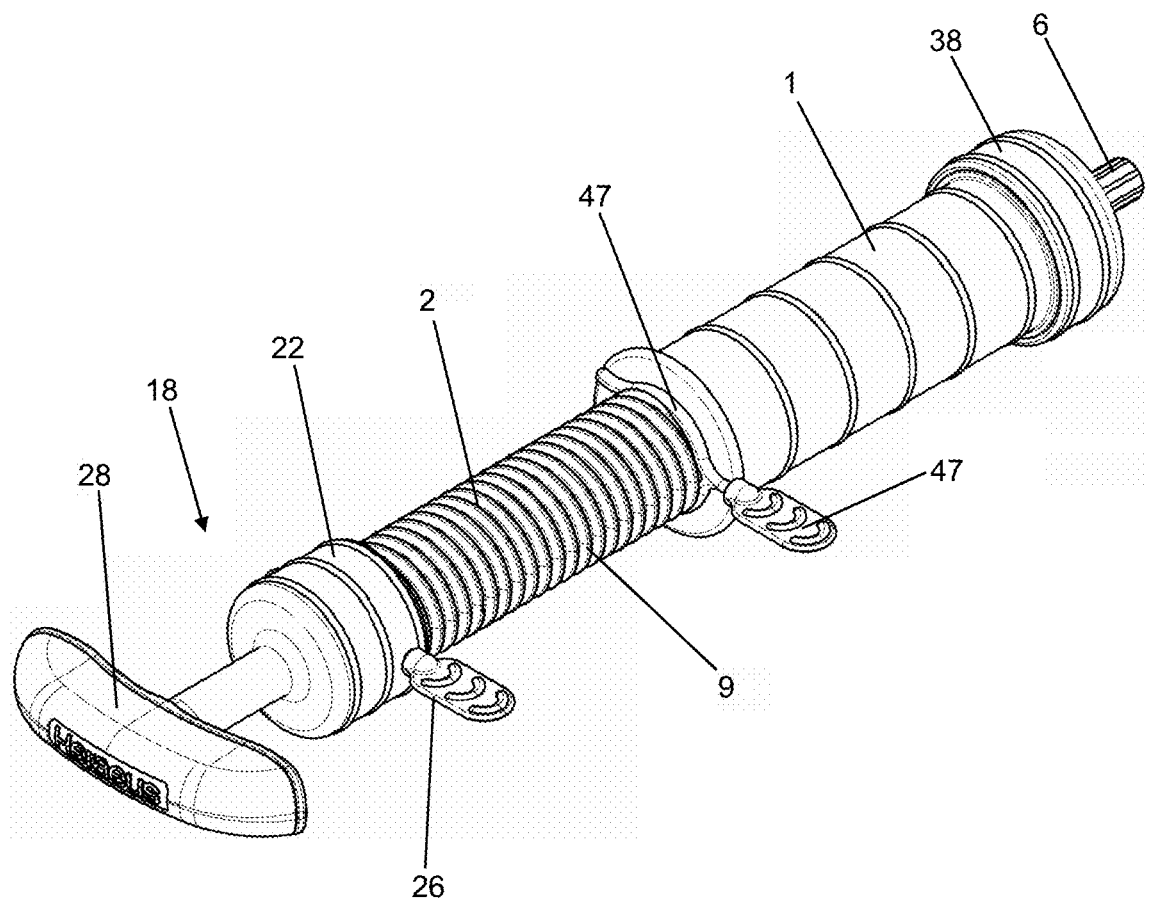
FIG. 3 shows another schematic perspective cross-sectional view of the first device as shown in FIGS. 1 and 2 having a second securing element.

Referring now to the drawing, in which like reference numbers refer to like elements throughout the various figures that comprise the drawing, FIGS. 1 to 8 show a first device according to one embodiment of the invention for the storage of the starting components 3, 4 of a bone cement dough 49 and for mixing of the bone cement dough 49. In this context, FIGS. 1 and 4 to 8 show the work-flow of a method according to the invention that is implemented using the first device, each shown in the form of a cross-sectional view.

The first device comprises a tube-shaped cartridge 1 made of plastic that forms a front part (on the bottom in FIGS. 1 and 4 to 8, on the top right in FIG. 2, and on the bottom left in FIG. 3) of the device. A rear-side rear part of the device is formed by a monomer receptacle 2. The device is intended for the production of a bone cement dough 49 (see FIGS. 7 and 8) that is produced from a monomer liquid 3 and from a cement powder 4. For this purpose, the monomer liquid 3 is contained in an ampoule 5 that can be fractured and is made of glass or plastic as the monomer liquid container for the monomer liquid 3, whereby the ampoule 5 is plugged into the monomer receptacle 2. The cartridge 1 forms a cylindrical internal space 11 on its inside that contains the cement powder 4.

The cartridge 1 comprises, on its front side (on the bottom in FIGS. 1 and 4 to 8, on the top right in FIG. 2, and on the bottom left in FIG. 3), a dispensing opening that is initially closed by a removable closure or stopper 6. Multiple gas supply openings 7 through which a gas can be aspirated from the inside of the device and through which a sterilizing gas such as ethylene oxide can be delivered for sterilization of the inside of the device are situated in the side wall of the monomer receptacle 2.

An internal thread 8 is situated in the rear-side end of the cartridge 1. The monomer receptacle 2 comprises, on its outside, an external thread 9 that fits with the internal thread 8 of the cartridge 1. The monomer receptacle 2 is shaped as a threaded tube and comprises, on its inside, a cylindrical chamber 10 into which the ampoule 5 is plugged. For this purpose, the ampoule 5 comprises a cylindrical ampoule body with a fitting diameter. On the inside of the cartridge 1, the cartridge 1 forms the cylindrical internal space 11. The cylindrical geometry of the internal space 11 and of the chamber 10 corresponds to cylinders with a circular base surface.

The monomer receptacle 2 is bordered, on its front side, by a cylindrical plunger 12 that closes the chamber 10 toward the front at its circular base surface. The plunger 12 comprises multiple channels 14 as a passage through the plunger 12, which are arranged in a ring-shape in the plunger 12 and connect the front side of the plunger 12 to the rear side of the plunger 12 and thereby connect the chamber 10 of the monomer receptacle 2 to the internal space 11 of the cartridge 1. The channels 14 are covered by a ring-shaped pore filter 16. The pore filter 16 is impermeable to the cement powder 4 from the internal space 11 of the cartridge 1, and is permeable to the monomer liquid 3 and gases. By this configuration, the cement powder 4 is prevented from advancing into the chamber 10 of the monomer receptacle 2. The plunger 12 comprises a larger external diameter than the external thread 9 of the monomer receptacle 2. The external diameter of the cylindrical plunger 12 fits the internal diameter of the internal space 11 of the cartridge 1. During the assembly of the device, the monomer receptacle 2 must be plugged into the cartridge 1 from the front and must be screwed, by the external thread 9, into the internal thread 8 of the cartridge 1. The plunger 12 of the monomer receptacle 2 seals the internal space 11 of the cartridge 1 in the direction of the rear side (on the top in FIGS. 1 and 4 to 8, on the bottom left in FIG. 2, and on the top right in FIG. 3).

An opening facility 18 is provided on the rear side of the monomer receptacle 2 and can be used to push the ampoule 5 in the direction of the plunger 12 in order to open the ampoule 5 and to open the monomer liquid 3 on the inside of the chamber 10. For this purpose, the opening facility 18 comprises a hollow cylinder 20 that is shaped in the form of a sleeve. In this context, the hollow cylinder 20 touches against the internal wall of the chamber 10 and covers it in the area of the rear side of the chamber 10. A closed wall 21 is provided in the hollow cylinder 20 such as to be vertical with respect to the axis of the cylinder geometry of the hollow cylinder 20 such that the hollow cylinder 20 with the closed wall 21 closes the chamber 10, on its rear side, with respect to the outside. The hollow cylinder 20 is attached to a screw-type closure cap 22. The lateral cylinder wall (the cylinder jacket surface) of the hollow cylinder 20 has radial boreholes 23 provided in it that are flush with the gas supply openings 7 in the starting state and storage state of the device (see FIG. 1). By this configuration, the chamber 10 and thereby, through the channels 14, the internal space 11 of the cartridge 1 as well, and thereby the cement powder 4 are connected in a gas-permeable manner to the surroundings of the device in this state. The closure cap 22 comprises an internal thread 24 that fits the external thread 9 of the monomer receptacle 2.

The closure cap 22, or the opening facility 18 as it may be, is screwed a way, but not all the way to a limit stop, onto the rear side of the monomer receptacle 2 and is thus attached to same. It is important that the closure cap 22 can be screwed further onto the monomer receptacle 2 and that the hollow cylinder 20 can thus be inserted more deeply into the chamber 10.

A through-going borehole, into which a securing element 26 in the form of a pin is plugged and is secured from falling out by a holder cap 27, is provided on the rear side of the monomer receptacle 2 and behind the closed wall 21 of the hollow cylinder 20. The securing element 26 prevents the closure cap 22 from being screwed in or out inadvertently and thus prevents the opening facility 18 from being operated inadvertently. The securing element 26 can be released right before a use of the device by pulling off the holder cap 27 and pulling out the pin. The opening facility 18 can then be screwed into the chamber 10.

When the opening facility 18 is being screwed in, the boreholes 23 are rotated away from the gas supply openings 7 and are shifted in a longitudinal direction and are closed by the external wall of the hollow cylinder 20. This action closes the device with respect to the outside such that the monomer liquid 3 exiting into the chamber 10 cannot exit from the chamber 10 through the gas supply openings 7.

In order to prevent the closure cap 22 from rotating in the wrong direction and thus to prevent the chamber 10 from being opened on its rear side, a reverse motion lock 47 is provided (shown in FIG. 1). The reverse motion lock 47 prevents the closure cap 22 from being released and/or the opening facility 18 from being released from the monomer receptacle 2. The reverse motion lock 47 can be implemented, for example, as a screw lock in the form of a locking disk or by a pair of wedge lock disks or similar measures. The reverse motion lock 47 not only prevents the opening facility 18 from being released, but the reverse motion lock 47, if designed appropriately, can prevent the gas supply openings 7 from possibly being opened again by the opening facility 18 being screwed back.

In order to be able to conveniently rotate the opening facility 18 by hand, the rear side end thereof is provided with a handle 28. In order to be able to close the gas supply opening 7 in a gas-tight and pressure-tight manner and to seal the hollow cylinder 20 with respect to the internal wall of the chamber 10, two circumferential seals 30 made of rubber are arranged in circumferential grooves on the external circumference of the hollow cylinder 20. The radial boreholes 23 are arranged between the seals 30, which are situated at a distance from each other in a longitudinal direction. The rear-side seal of the two seals 30 is arranged close to the boreholes 23 such that the gas supply openings 7 are closed rapidly during an axial motion of the hollow cylinder 20 in the longitudinal direction. Alternatively, sealing rings can just as well be arranged about the gas supply openings 7 on the internal wall of the monomer receptacle 2 or about the boreholes 23 on the external wall of the hollow cylinder 20. The gas supply openings 7 are sealed by the rear seal (on the top in FIG. 1), when the hollow cylinder 20 is being pushed in the direction of the plunger 12 (see FIG. 3).

Likewise, the external circumference of the plunger 12 has two grooves arranged on it, in which two circumferential seals 32 made of rubber are situated and which are situated at a distance from each other in the longitudinal direction. The seals 32 seal the plunger 12 with respect to the internal space 11 of the cartridge 1 and close the rear side of the internal space 11 of the cartridge 1.

The channels 14 and the ring-shaped pore filter 16 are arranged about a mandrel 34 for fracturing the ampoule 5. For this purpose, the mandrel 34 points into the inside of the chamber 10. For this purpose, the ampoule 5 can be pushed onto the mandrel 34 by the hollow cylinder 20 until the bottom of the ampoule 5 fractures. For this purpose, the hollow cylinder 20 has approximately the same diameter as the ampoule body of the ampoule 5. An ampoule head of the ampoule 5 is arranged on the inside of the hollow cylinder 20 in this context. What this attains is that the ampoule 5 is not fractured in the area of the hollow cylinder 20, since the cylindrical ampoule body is very stable, whereas the mandrel 34 can be pushed relatively easily into the bottom of the ampoule 5.

To make sure that the ampoule 5 is not opened during the transport of the device, a spring 36 is arranged about the mandrel 34 in the chamber 10 and positions the ampoule 5 at a distance from the mandrel 34. When the opening facility 18 is being screwed inwards, the spring 36 is compressed by the ampoule 5 and the bottom of the ampoule 5 is fractured on the mandrel 34.

The front side of the cartridge 1 is closed by a cartridge lid 38. A socket 39 bordering the dispensing opening on the front side is formed in the middle of the cartridge lid 38. The stopper 6 closing the dispensing opening is attached to the socket 39 such that it can be released. The cartridge lid 38 is screwed onto an external thread 42 on the front side of the cartridge 1 by an internal thread 40. The cartridge lid 38 is additionally sealed with respect to the cartridge 1 by a circumferential seal 44.

The internal space of the cartridge contains seven loose beads 45 made of zirconium dioxide ceramics as mixing elements. The beads 45 allow the content of the internal space 11 of the cartridge 1 to be mixed by shaking the device. Since the beads 45 have a higher density than the bone cement dough 49, they can be moved in the bone cement dough 49 and even significantly better in a bone cement dough-gas mixture 48 (see FIG. 6) by shaking the device against the bone cement dough 49 and/or the bone cement dough-gas mixture 48. In this context, the beads 45 fly about in the internal space 11 of the cartridge 1 and mix the starting components 3, 4 in the process.

To make sure that the beads 45 cannot close the dispensing opening, multiple projecting fins 46 are provided on the inside of the cartridge lid 38 and extend in a radial direction from the edge of the internal wall of the internal space 11 in the direction of the dispensing opening. The fins 46 are tapered down in the radial direction towards the outside such that the beads 45 slide or roll away from the dispensing opening when the plunger 12 and the bone cement dough 49 are advanced outwards (see FIGS. 7 and 8). If a bead 45 is positioned exactly centrally in front of the dispensing opening, it is kept at a distance from the dispensing opening even then by the fins 46 such that the bone cement dough 49 can flow through between the bead 45 and the fins 46 into and through the dispensing opening.

A second securing element in the form of a brace 47 can be arranged on the transition from the monomer receptacle 2 into the cartridge 1. The brace 47 can be used to prevent the monomer receptacle 2 from being screwed into the cartridge 1. The brace 47 is pulled off before the monomer receptacle 2 is screwed into the cartridge 1. The brace 47 is not particularly significant and can be omitted just as well.

The work-flow of a method according to the invention is discussed in the following based on FIGS. 1 to 8. Initially, the device is in the starting state (see FIGS. 1 to 3). In this state, the device has been packaged and sterilized with ethylene oxide. The ethylene oxide can enter into the chamber 10 through the gas supply openings 7 and the boreholes 23, and can enter into the internal space 11 of the cartridge 1 through the pore filter 16 and the channels 14. The gas exchange takes place in a vacuum chamber or in a negative pressure chamber in this context. In this state (see FIG. 3), the device is unpacked.

The brace 47 is pulled off first. But this action can also take place at a later time. The device is now in the state shown in FIGS. 1 and 2. Subsequently, the monomer receptacle 2 is screwed into the cartridge 1. In this context, any supernatant gas is pushed from the internal space 11 of the cartridge 1 through the passage formed by the channels 14 and through the pore filter 16 into the chamber 10. The gas from the chamber 10 ultimately escapes through the bore holes 23 and the gas supply openings 7.

Figure 4:
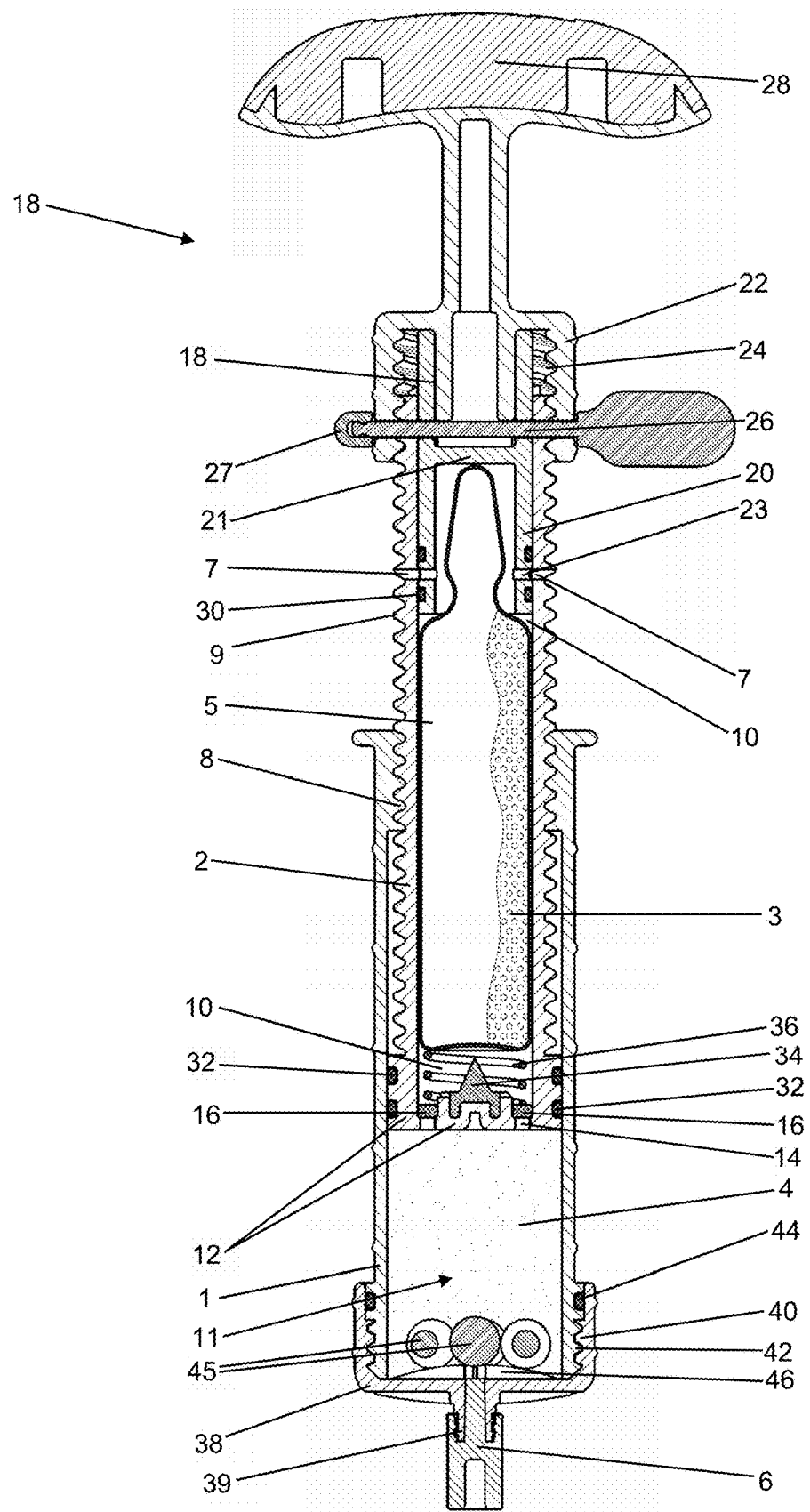
FIG. 4 shows a schematic cross-sectional view of the first device as shown in FIGS. 1 through 3 having a screwed-in monomer receptacle for illustration of the work-flow of a method according to the invention.

Ultimately, the cement powder 4 in the internal space 11 of the cartridge 1 is compressed and gas is present only between the powder particles. This state is shown in FIG. 4.

Figure 5:
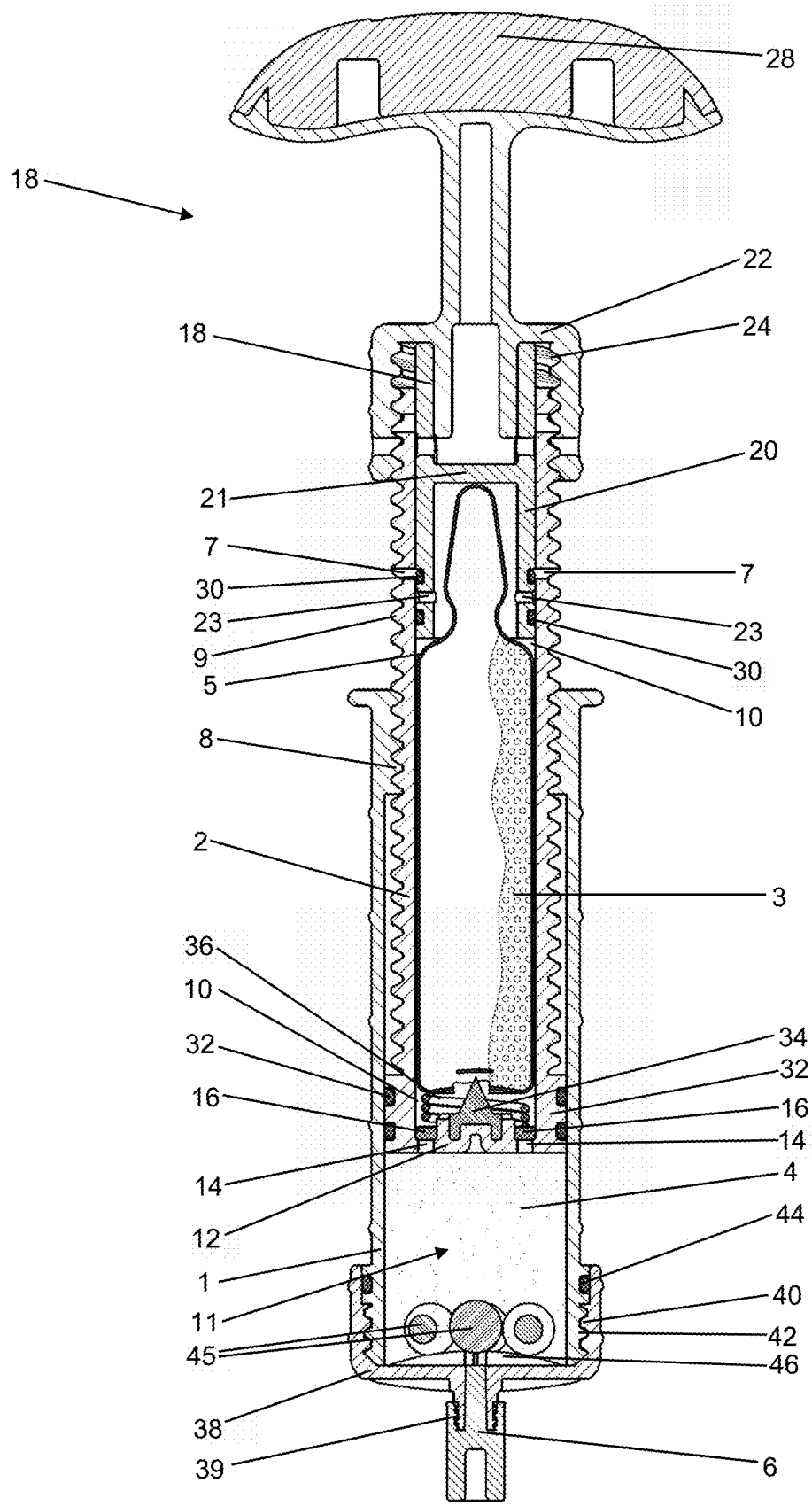
FIG. 5 shows a schematic cross-sectional view of the first device as shown in FIGS. 1 through 4 having an opened monomer liquid container for illustration of the work-flow of the method according to the invention.

In a next step, the securing element 26 is removed and the opening facility 18 is screwed into the chamber 10. It is preferred to hold the device with the cartridge lid 38 downwards in this context. The hollow cylinder pushes the shoulders of the ampoule 5 against the force of the spring 36 in the direction of the mandrel 34 in this context. The gas supply openings 7 are closed by the screw motion of the hollow cylinder 20. Subsequently, the bottom of the ampoule 5 is pushed onto the mandrel 34 and the ampoule 5 fractures on its bottom. This state is shown in FIG. 5.

The monomer liquid 3 exits from the bottom of the ampoule 5 in the area of the passage formed by the channels 14. Since the device is held with the cartridge lid 38 downwards, the monomer liquid 3 driven by gravity immediately flows downwards through the pore filter 16 and the channels 14 into the internal space 11 of the cartridge 1 and distributes in the cement powder 4. In order to accelerate the monomer transfer, the monomer receptacle 2 is unscrewed from the cartridge 1 again. Since the gas supply openings 7 are closed in a gas-tight and pressure-tight manner and the internal space 11 of the cartridge 1 is sealed with respect to the plunger 12 and is closed with respect to the outside, the increase of the volume of the internal space 11 of the cartridge 1 generates a negative pressure in the internal space 11 of the cartridge 1 by which the monomer liquid 3 is aspirated into the internal space 11 of the cartridge 1. As before, the device is held with the cartridge lid 38 downwards. Moreover, the increase of the internal space 11 of the cartridge 1 also reduces the gas pressure on the inside of the device. The gas at negative pressure is ultimately also present in the internal space 11 of the cartridge 1, over the starting components 3, 4. In this context, the volume of the supernatant gas is at least twice the volume of the monomer liquid 3.

Figure 6:
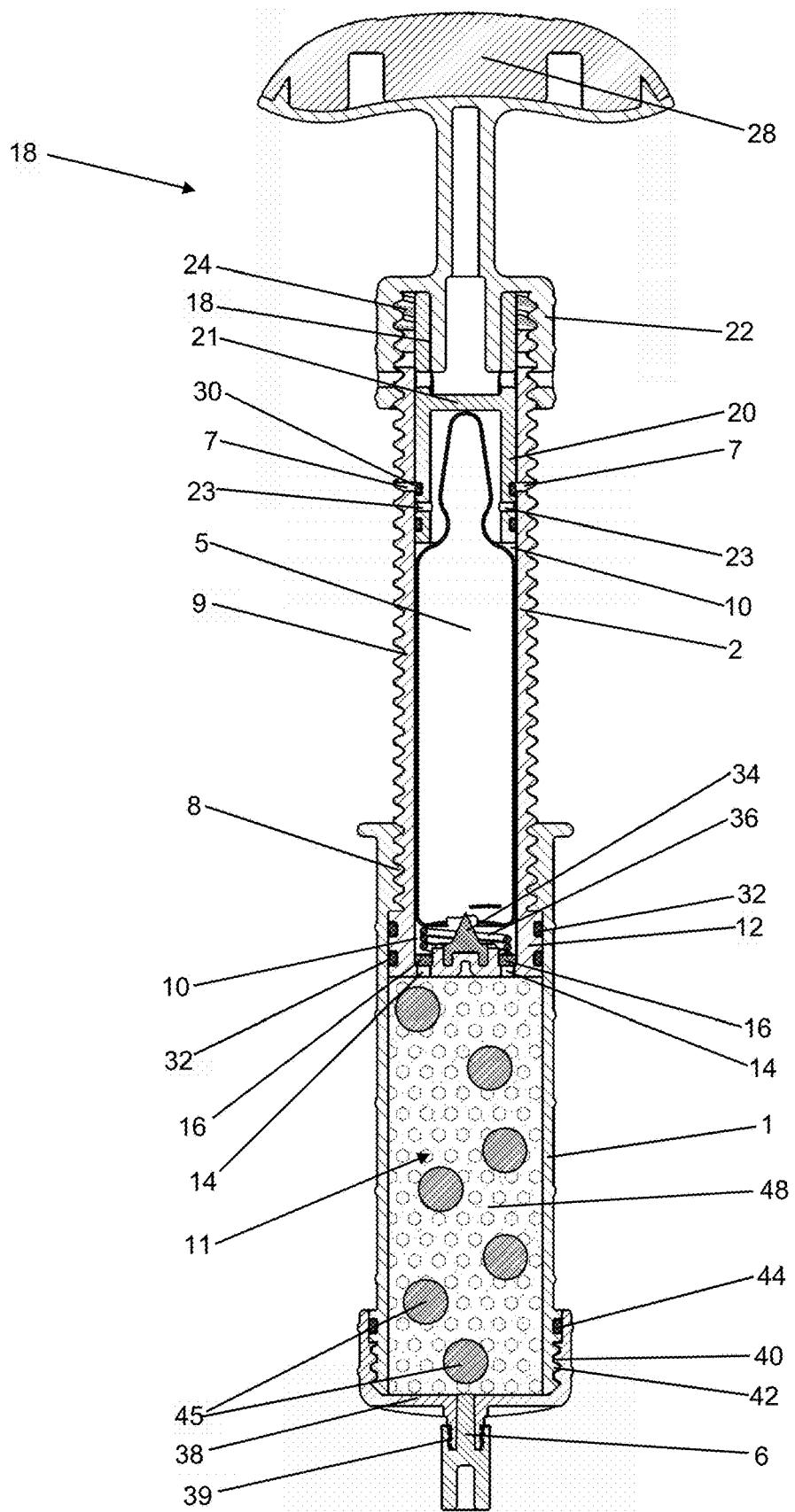
FIG. 6 shows a schematic cross-sectional view of the first device as shown in FIGS. 1 through 5 with the monomer receptacle unscrewed and monomer liquid drawn in for illustration of the work-flow of the method according to the invention.

The contents of the internal space 11 of the cartridge 1, namely the monomer liquid 3 and the cement powder 4, can be mixed by shaking the device in this state. In this context, the beads 45 fly about in the internal space 11 of the cartridge 1 and thus support the mixing of the components. The internal space 11 of the cartridge 1 then contains the bone cement dough-gas mixture 48. This state is shown in FIG. 6. The bone cement dough 49 is mixed well after repeated shaking.

Figure 7:
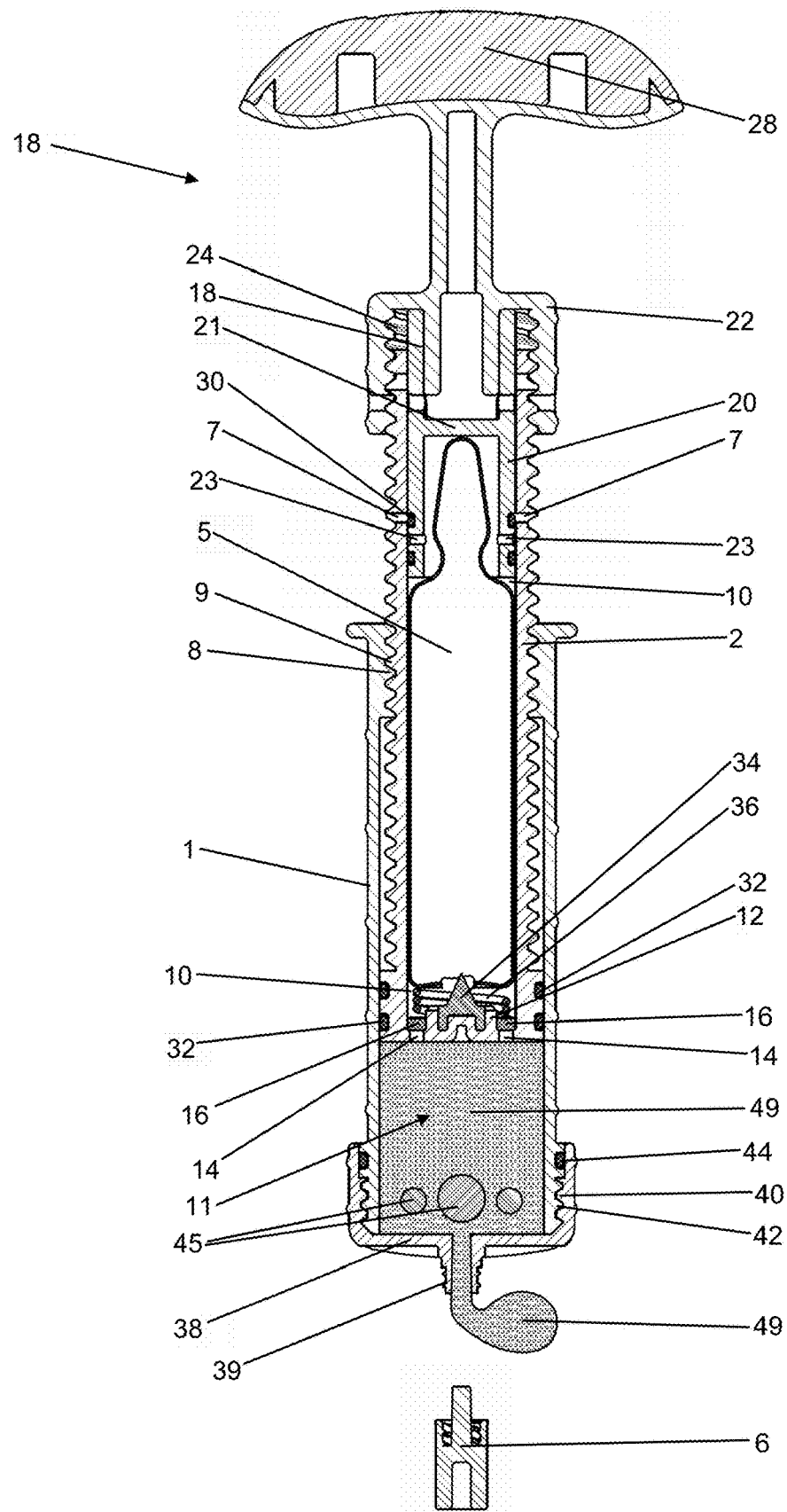
FIG. 7 shows a schematic cross-sectional view of the first device as shown in FIGS. 1 through 6 with the monomer receptacle screwed in and excess gas pushed out for illustration of the work-flow of the method according to the invention.

The device is then reversed such that the cartridge lid 38 faces upwards. The stopper 6 is removed from the dispensing opening. Now, as an option, a hose with a trocar (not shown) can be attached to the socket 39 through which the bone cement dough 49 can be applied under X-ray control in places that are difficult to access. Since the bone cement dough 49 for use in spondylodesis is rather inviscid, the gas bubbles rise. The monomer receptacle 2 is screwed into the cartridge 1 again and the gas escapes in an upward direction out of the dispensing opening. Lastly, the bone cement dough 49 exits through the dispensing opening and/or through the socket 39 from the internal space 11 of the cartridge 1. This state is shown in FIG. 7.

Figure 8:
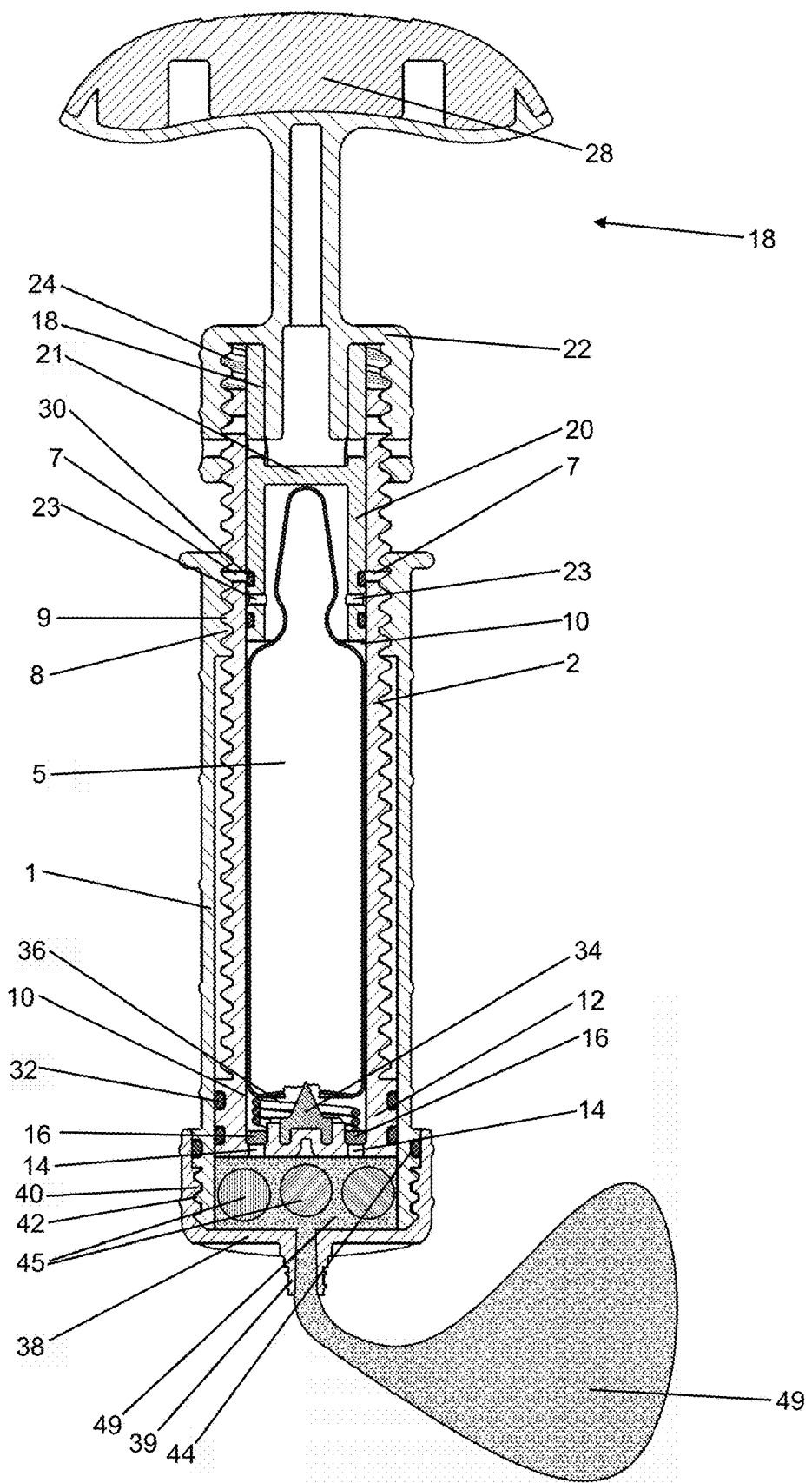
FIG. 8 shows a schematic cross-sectional view of the first device as shown in FIGS. 1 through 7 during the dispensation of the bone cement dough produced for illustration of the work-flow of the method according to the invention.

Screwing the monomer receptacle 2 further into the cartridge 1, the plunger 12 extrudes the bone cement dough 49 from the device. Lastly, the plunger 12 pushes the beads 45 against the cartridge lid 38. This completes the extrusion process. This state is shown in FIG. 8.

Figure 9:
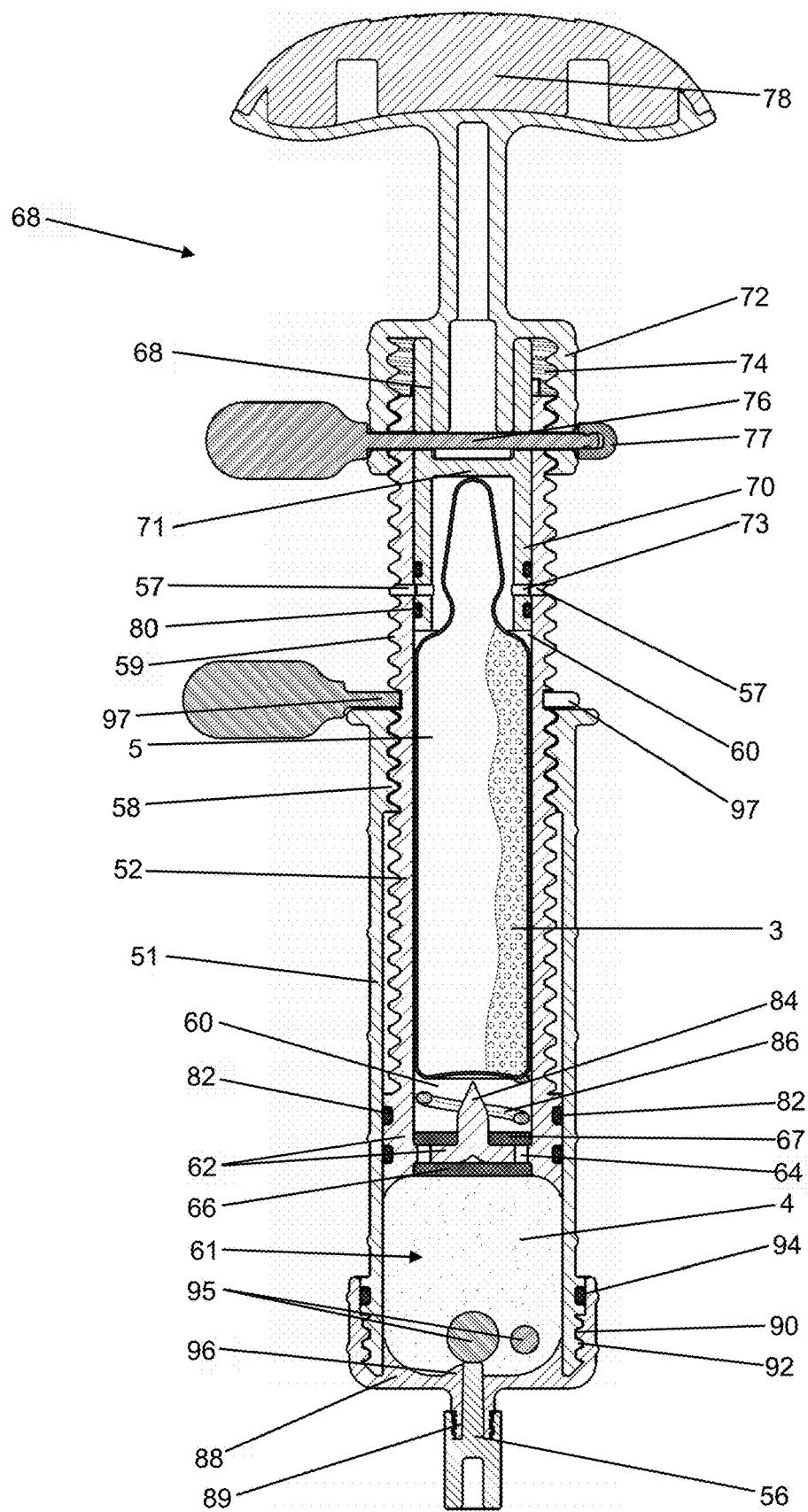
FIG. 9 shows a cross-sectional view of an exemplary second device according to another embodiment of the invention for production of a bone cement dough.
Figure 10:
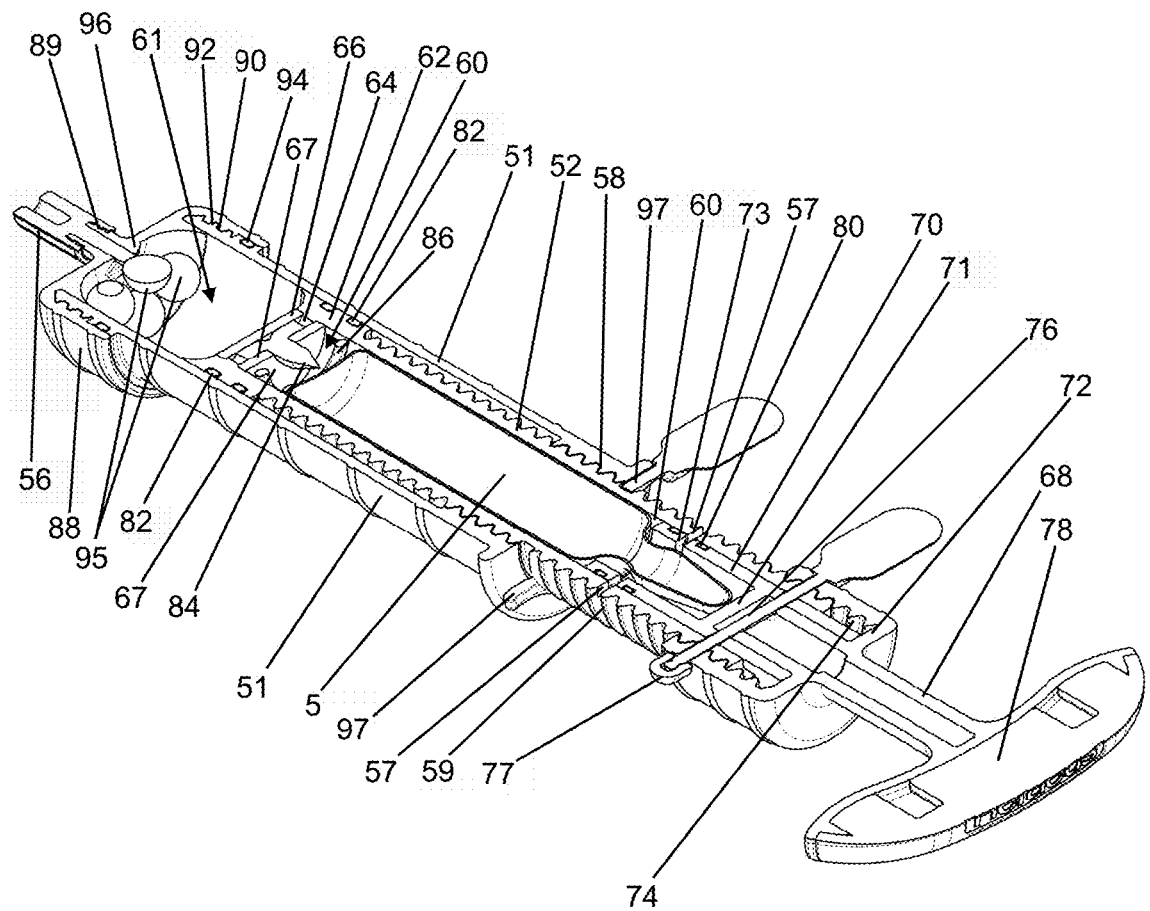
FIG. 10 shows a schematic perspective sectional view of the second device as shown in FIG. 9 for the production of a bone cement dough in the absence of the starting components.

FIGS. 9 and 10 show a second embodiment of the device according to the invention for the storage of the starting components 3, 4 of a bone cement dough and for the mixing of the bone cement dough. Accordingly, FIG. 9 shows a cross-sectional view of the starting state and FIG. 10 shows a perspective cross-sectional view of the device without the starting components contained in it.

The second embodiment of the device according to the invention comprises a tube-shaped cartridge 51 made of plastic that forms a front part (on the bottom in FIG. 9 and on the top left in FIG. 10) of the device. A rear-side rear part of the device is formed by a monomer receptacle 52. The device is intended for the production of a bone cement dough that is produced from a monomer liquid 3 and from a cement powder 4. For this purpose, the monomer liquid 3 is contained in an ampoule 5 that can be fractured and is made of glass or plastic as the monomer liquid container for the monomer liquid 3, whereby the ampoule 5 is plugged into the monomer receptacle 52. The cartridge 51 forms a cylindrical internal space 61 on its inside that contains the cement powder 4.

The cartridge 51 comprises, on its front side (on the bottom in FIG. 9 and on the top left in FIG. 10), a dispensing opening that is initially closed by a removable closure or stopper 56. Multiple gas supply openings 57 through which a gas can be aspirated from the inside of the device and through which a sterilizing gas such as ethylene oxide can be added for sterilization of the inside of the device are situated in the side wall of the monomer receptacle 52.

An internal thread 58 is situated in the rear-side end of the cartridge 51. The monomer receptacle 52 comprises, on its outside, an external thread 59 that fits with the internal thread 58 of the cartridge 51. The monomer receptacle 52 is shaped like a threaded tube and comprises, on its inside, a cylindrical chamber 60 into which the ampoule 5 is plugged. For this purpose, the ampoule 5 comprises a cylindrical ampoule body with a fitting diameter. On the inside of the cartridge 51, the cartridge 51 forms the cylindrical internal space 61. The cylindrical geometry of the internal space 61 and of the chamber 60 corresponds to cylinders with a circular base surface.

The monomer receptacle 52 is bordered, on its front side, by a cylindrical plunger 62 that closes the chamber 60 toward the front at its circular base surface. The plunger 62 comprises multiple channels 64 as a passage through the plunger 62, which are arranged in a ring-shape in the plunger 62 and connect the front side of the plunger 62 to the rear side of the plunger 62 and thereby connect the chamber 60 of the monomer receptacle 52 to the internal space 61 of the cartridge 51. The channels 64 are covered by a circular disk-shaped pore filter 66 and a ring-shaped mesh as a splinter protector 67. The pore filter 66 is impermeable to the cement powder 4 from the internal space 61 of the cartridge 51, and is permeable to the monomer liquid 3 and gases. By this configuration, the cement powder 4 is prevented from advancing into the chamber 60 of the monomer receptacle 2. The splinter protector 67 can be implemented by a mesh. The splinter protector 67 prevents any advancement of splinters of the opened ampoule 5 into the channels 64 of the passage. The plunger 62 comprises a larger external diameter than the external thread 59 of the monomer receptacle 52. The external diameter of the cylindrical plunger 62 fits the internal diameter of the internal space 61 of the cartridge 51. During the assembly of the device, the monomer receptacle 52 is plugged into the cartridge 51 from the front and is screwed, by the external thread 59, into the internal thread 58 of the cartridge 51. The plunger 62 of the monomer receptacle 52 seals the internal space 61 of the cartridge 51 in the direction of the rear side (on the top in FIG. 9 and on the bottom right in FIG. 10).

An opening facility 68 is provided on the rear side of the monomer receptacle 52 and can be used to push the ampoule 5 in the direction of the plunger 62 in order to open the ampoule 5 and to open the monomer liquid 3 on the inside of the chamber 60. For this purpose, the opening facility 68 comprises a hollow cylinder 70 that is shaped in the form of a sleeve. In this context, the hollow cylinder 70 touches against the internal wall of the chamber 60 and covers it in the area of the rear side of the chamber 60. A closed wall 71 is provided in the hollow cylinder 70 such as to be vertical with respect to the axis of the cylinder geometry of the hollow cylinder 70 such that the hollow cylinder 70 with the closed wall 71 closes the chamber 60, on its rear side, with respect to the outside. The hollow cylinder 70 is attached to a screw-type closure cap 72. The lateral cylinder wall (the cylinder jacket surface) of the hollow cylinder 70 has radial boreholes 73 provided in it that are flush with the gas supply openings 57 in the starting state and storage state of the device (see FIGS. 9 and 10). By this configuration, the chamber 60 and thereby, through the channels 64, the internal space 61 of the cartridge 51 as well, and thereby the cement powder 4 are connected in a gas-permeable manner to the surroundings of the device in this state. The closure cap 72 comprises an internal thread 74 that fits the external thread 59 of the monomer receptacle 52.

The closure cap 72, or the opening facility 68 as it may be, is screwed part way, but not all the way to a limit stop, onto the rear side of the monomer receptacle 52 and is thus attached to same. It is important that the closure cap 72 can be screwed further onto the monomer receptacle 52 and that the hollow cylinder 70 can thus be inserted more deeply into the chamber 60.

A through-going borehole, into which a securing element 76 in the form of a pin is plugged and is secured from falling out by a holder cap 77, is provided on the rear side of the monomer receptacle 52 and behind the closed wall 71 of the hollow cylinder 70. The securing element 76 prevents the closure cap 72 from being screwed in or out inadvertently and thus prevents the opening facility 68 from being operated inadvertently. The securing element 76 can be released right before a use of the device by pulling off the holder cap 77 and pulling out the pin. The opening facility 68 can then be screwed into the chamber 60.

When the opening facility 68 is screwed in, the boreholes 73 are rotated away from the gas supply openings 57 and are shifted in the longitudinal direction and are closed by the external wall of the hollow cylinder 70. This action closes the device with respect to the outside such that the monomer liquid 3 exiting into the chamber 60 cannot exit from the chamber 60 through the gas supply openings 57.

In order to prevent the closure cap 72 from rotating in the wrong direction and thus to prevent the chamber 60 from being opened on its rear side, a reverse motion lock is provided (not shown in FIGS. 9 and 10). The reverse motion lock prevents the closure cap 72 from being released and/or the opening facility 68 from being released from the monomer receptacle 52. The reverse motion lock can be implemented, for example, as a screw lock in the form of a locking disk or by a pair of wedge lock disks or similar mechanisms. The reverse motion lock not only prevents the opening facility from being released, but the reverse motion lock, if designed appropriately, can prevent the gas supply openings 57 from possibly being opened again by the opening facility 68 being screwed back.

In order to be able to conveniently rotate the opening facility 68 by hand, the rear side end thereof is provided with a handle 78. In order to be able to close the gas supply opening 57 in a gas-tight and pressure-tight manner and to seal the hollow cylinder 70 with respect to the internal wall of the chamber 60, two circumferential seals 80 made of rubber are arranged in circumferential grooves on the external circumference of the hollow cylinder 70. The radial boreholes 73 are arranged between the seals 80, which are situated at a distance from each other in the longitudinal direction. The rear-side seal of the two seals 80 is arranged close to the boreholes 73 such that the gas supply openings 57 are closed rapidly during an axial motion of the hollow cylinder 70 in the longitudinal direction. Alternatively, sealing rings can just as well be arranged about the gas supply openings 57 on the internal wall of the monomer receptacle 52 or about the boreholes 73 on the external wall of the hollow cylinder 70. The gas supply openings 57 are sealed by the rear seal (on the top in FIG. 9), when the hollow cylinder 70 is being pushed in the direction of the plunger 62.

Likewise, the external circumference of the plunger 62 has two grooves arranged on it, in which two circumferential seals 82 made of rubber are situated and which are situated at a distance from each other in the longitudinal direction. The seals 82 seal the plunger 62 with respect to the internal space 61 of the cartridge 51 and close the rear side of the internal space 61 of the cartridge 51.

The channels 64 and the ring-shaped pore filter 66 are arranged about a mandrel or cutting edge 84 for fracturing the ampoule 5. For this purpose, the mandrel or cutting edge 84 faces into the inside of the chamber 60. For this purpose, the ampoule 5 can be pushed onto the mandrel or cutting edge 84 by the hollow cylinder 70 until the bottom of the ampoule 5 fractures. For this purpose, the hollow cylinder 70 has approximately the same diameter as the ampoule body of the ampoule 5. An ampoule head of the ampoule 5 is arranged on the inside of the hollow cylinder 70 in this context. What this configuration attains is that the ampoule 5 is not fractured in the area of the hollow cylinder 70, since the cylindrical ampoule body is very stable, whereas the mandrel or cutting edge 84 can be pushed relatively easily into the bottom of the ampoule 5.

To make sure that the ampoule 5 is not opened during the transport of the device, a spring 86 is arranged about the mandrel or cutting edge 84 in the chamber 60 and positions the ampoule 5 at a distance from the mandrel or cutting edge 84. When the opening facility 68 is screwed inwards, the spring 86 is compressed by the ampoule 5 and the bottom of the ampoule 5 is fractured on the mandrel or cutting edge 84.

The front side of the cartridge 51 is closed by a cartridge lid 88. A socket 89 bordering the dispensing opening on the front side is formed in the middle of the cartridge lid 88. The stopper 56 closing the dispensing opening is attached to the socket 89 such that it can be released. The cartridge lid 88 is screwed onto an external thread 92 on the front side of the cartridge 51 by an internal thread 90. The cartridge lid 88 is additionally sealed with respect to the cartridge 51 by a circumferential seal 94.

The internal space 61 of the cartridge 51 contains several loose beads 95 made of zirconium dioxide ceramics as mixing elements. The beads 95 allow the content of the internal space 61 of the cartridge 51 to be mixed by shaking the device. Since the beads 95 have a higher density than the bone cement dough, they can be moved in the bone cement dough and even significantly better in a bone cement dough-gas mixture by shaking the device against the bone cement dough and/or the bone cement dough-gas mixture. In this context, the beads 95 fly about in the internal space 61 of the cartridge 51 and mix the starting components 3, 4 in the process.

To make sure that the beads 95 cannot close the dispensing opening, a projecting fin 96, which elevates right next to the dispensing opening, is provided on the inside of the cartridge lid 88. If a bead 95 is positioned centrally in front of the dispensing opening, it is pushed to the side by the fin 96 and cannot touch flush against the dispensing opening such that the bone cement dough can flow through between the beads 95 and the fin 96 into and through the dispensing opening.

The front side of the plunger 62 and the rear side of the cartridge lid 88, which border the front sides of the internal space 61 of the cartridge 51, comprise flanks that rise toward the side wall of the internal space 61 of the cartridge 51 and have a radius of curvature that is larger than the radius of the beads 95. By this configuration, the beads 95 can reach any area of the internal space 61 when the device is shaken. This prevents edges from being present in the internal space 61, in which the cement powder 4 cannot be reached by the beads 95 and thus cannot be mixed into the bone cement dough.

A second securing element in the form of a brace 97 can be arranged on the transition from the monomer receptacle 52 into the cartridge 51. The brace 97 can be used to prevent the monomer receptacle 52 from being screwed into the cartridge 51. The brace 97 is pulled off before the monomer receptacle 52 is screwed into the cartridge 51. The brace 97 is not particularly significant and can be omitted just as well.

The work-flow of a method according to the invention is illustrated in the following. Initially, the device is in the starting state (see FIGS. 9 and 10). In this state, the device has been packaged and sterilized with ethylene oxide. The ethylene oxide can enter into the chamber 60 through the gas supply openings 57 and the boreholes 73, and can enter into the internal space 61 of the cartridge 51 through the pore filter 66, the splinter protector 67, and the channels 64. The gas exchange takes place in a vacuum chamber or in a negative pressure chamber in this context. In this state (see FIGS. 9 and 10), the device is being unpacked.

The brace 97 is pulled off first. But this can also take place at a later time. The device is now in the state shown in FIG. 9. In the second embodiment of the device according to the invention, the monomer receptacle 52 does not need to be screwed into the cartridge 51 initially, since the device is already in the maximally screwed-in state (see FIGS. 9 and 10). From here, the method proceeds mostly analogous to the method described with regard to the first exemplary embodiment according to FIGS. 1 to 8.

In a next step, the securing element 76 is removed and the opening facility 68 is screwed into the chamber 60. It is preferred to hold the device with the cartridge lid 88 downwards in this context. The hollow cylinder pushes the shoulders of the ampoule 5 against the force of the spring 86 in the direction of the mandrel or cutting edge 84 in this context. The gas supply openings 57 are closed by the screw motion of the hollow cylinder 70. Subsequently, the bottom of the ampoule 5 is pushed onto the mandrel or cutting edge 84 and the ampoule 5 fractures on its bottom.

The monomer liquid 3 exits on the bottom of the ampoule 5 in the area of the passage formed by the channels 64. Since the device is being held with the cartridge lid 88 downwards, the monomer liquid 3 driven by gravity immediately flows downwards through the splinter protector 67, the channels 64, and the pore filter 66 into the internal space 61 of the cartridge 51 and distributes in the cement powder 4. Splinters of the ampoule 5, if any, are retained by the splinter protector 67. In order to accelerate the monomer transfer, the monomer receptacle 52 is unscrewed from the cartridge 51. Since the gas supply openings 57 are closed in a gas-tight and pressure-tight manner and the internal space 61 of the cartridge 51 is sealed with respect to the plunger 62 and is closed with respect to the outside, the increase of the volume of the internal space 61 of the cartridge 51 generates a negative pressure in the internal space 61 of the cartridge 51 by which the monomer liquid 3 is aspirated into the internal space 61 of the cartridge 51. As before, the device is held with the cartridge lid 88 downwards. Moreover, the increase of the internal space 61 of the cartridge 51 also reduces the gas pressure on the inside of the device. The gas at negative pressure is ultimately also present in the internal space 61 of the cartridge 51, over the starting components 3, 4. In this context, the volume of the supernatant gas is at least twice the volume of the monomer liquid 3.

The content of the internal space 61 of the cartridge 51, namely the monomer liquid 3 and the cement powder 4, can be mixed by shaking the device in this state. In the process, the beads 95 fly about in the internal space 61 of the cartridge 51 and thus support the mixing of the components, whereby all areas are reached due to the bordering of the internal space 61 of the cartridge 51 having a rounded shape such that complete mixing is attained. The internal space 61 of the cartridge 51 then contains a bone cement dough-gas mixture. The bone cement dough is mixed well after repeated shaking.

The device is then reversed such that the cartridge lid 88 faces upwards. The stopper 56 is removed from the dispensing opening. Now, as an option, a hose with a trocar (not shown) can be attached to the socket 89 through which the bone cement dough can be applied under X-ray control in places that are difficult to access. Since the bone cement dough for use in spondylodesis is rather inviscid, the gas bubbles rise. The monomer receptacle 52 is screwed into the cartridge 51 again and the gas escapes in the upward direction out of the dispensing opening. Lastly, the bone cement dough exits through the dispensing opening and/or through the socket 89 from the internal space 61 of the cartridge 51.

Screwing the monomer receptacle 52 further into the cartridge 51, the plunger 62 extrudes the bone cement dough from the device. Lastly, the plunger 62 pushes the beads 95 against the cartridge lid 88. This action completes the extrusion process.

Figure 11:
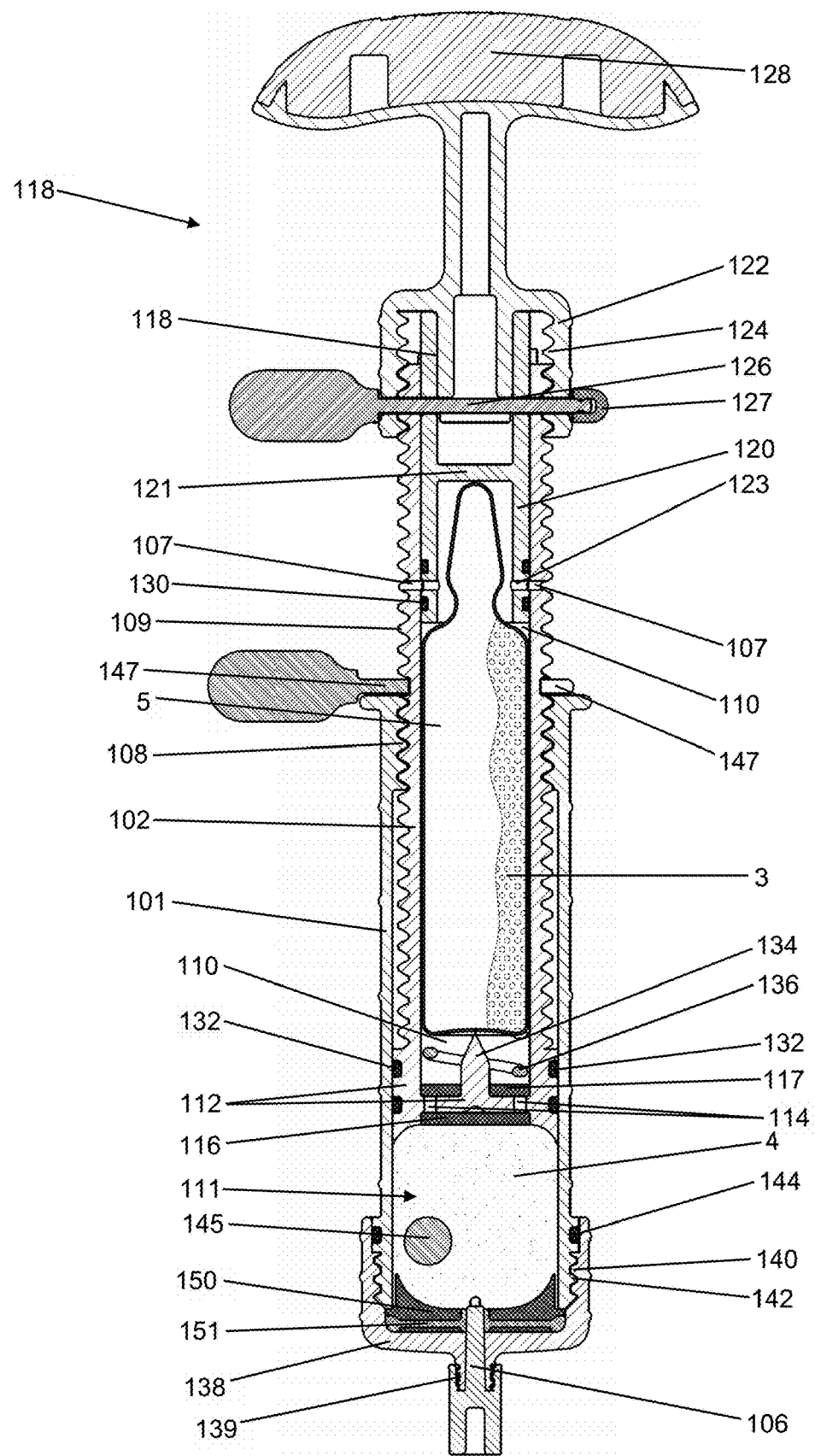
FIG. 11 shows a schematic cross-sectional view of a third exemplary device according to yet another embodiment of the invention for the production of a bone cement dough.
Figure 12:
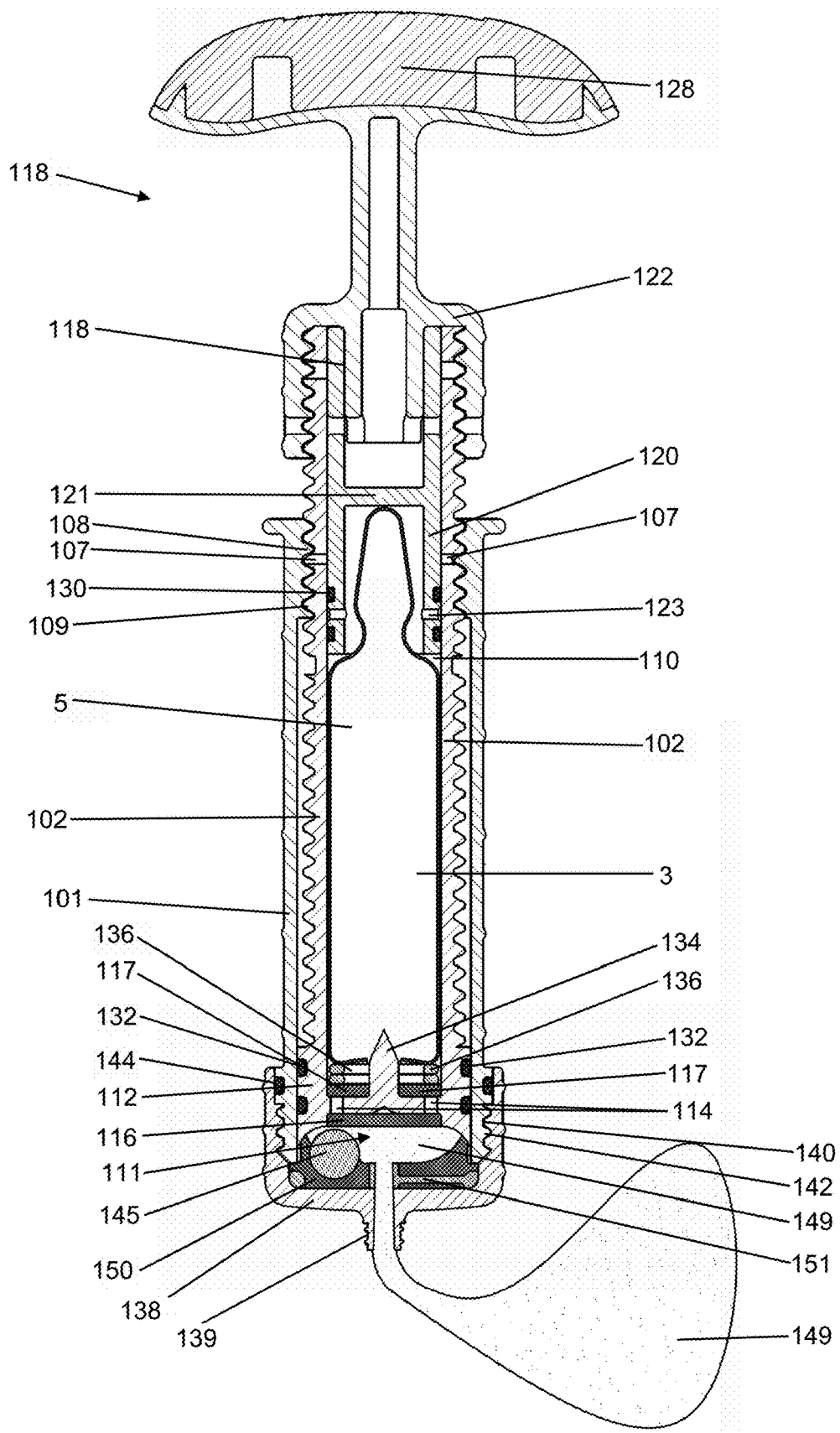
FIG. 12 shows a schematic cross-sectional view of the third device as shown in FIG. 11 during the dispensation of the bone cement dough thus produced.

FIGS. 11 and 12 show a third embodiment of the device according to the invention for the storage of the starting components 3, 4 of a bone cement dough 149 and for the mixing of the bone cement dough 149. In this context, FIG. 11 shows a cross-sectional view of the starting state, and FIG. 10 shows a cross-sectional view of the end state after exclusion of the ready-mixed bone cement dough 149.

The third embodiment of the device according to the invention comprises a tube-shaped cartridge 101 made of plastics that forms a front part (on the bottom in FIGS. 11 and 12) of the device. A rear-side rear part of the device is formed by a monomer receptacle 102. The device is intended for the production of a bone cement dough 149 that is produced from a monomer liquid 3 and from a cement powder 4. For this purpose, the monomer liquid 3 is contained in an ampoule 5 that can be fractured and is made of glass or plastic as the monomer liquid container for the monomer liquid 3, whereby the ampoule 5 is plugged into the monomer receptacle 102. The cartridge 101 forms a cylindrical internal space 111 on its inside that contains the cement powder 4.

The cartridge 101 comprises, on its front side (on the bottom in FIGS. 11 and 12), a dispensing opening that is initially closed by a removable closure or stopper 106. Multiple gas supply openings 107 through which a gas can be aspirated from the inside of the device and through which a sterilizing gas such as ethylene oxide can be added for sterilization of the inside of the device are situated in the side wall of the monomer receptacle 102.

An internal thread 108 is situated in the rear-side end of the cartridge 101. The monomer receptacle 102 comprises, on its outside, an external thread 109 that fits with the internal thread 108 of the cartridge 101. The monomer receptacle 102 is shaped like a threaded tube and comprises, on its inside, a cylindrical chamber 110 into which the ampoule 5 is plugged. For this purpose, the ampoule 5 comprises a cylindrical ampoule body with a fitting diameter. On the inside of the cartridge 101, the cartridge 101 forms the cylindrical internal space 111. The cylindrical geometry of the internal space 111 and of the chamber 110 corresponds to cylinders with a circular base surface.

The monomer receptacle 102 is bordered, on its front side, by a cylindrical plunger 112 that closes the chamber 110 toward the front at its circular base surface. The plunger 112 comprises multiple channels 114 as a passage through the plunger 112, which are arranged in a ring-shape in the plunger 112 and connect the front side of the plunger 112 to the rear side of the plunger 112 and thereby connect the chamber 110 of the monomer receptacle 102 to the internal space 111 of the cartridge 101. The channels 114 are covered by a circular disk-shaped pore filter 116 and a ring-shaped mesh as a splinter protector 117. The pore filter 116 is impermeable to the cement powder 4 from the internal space 111 of the cartridge 101, and is permeable to the monomer liquid 3 and gases. By this configuration, the cement powder 4 is prevented from advancing into the chamber 110 of the monomer receptacle 2. The splinter protector 117 can be implemented by a mesh. The splinter protector 117 prevents any advancement of splinters of the opened ampoule 5 into the channels 114 of the passage. The plunger 112 comprises a larger external diameter than the external thread 109 of the monomer receptacle 102. The external diameter of the cylindrical plunger 112 fits the internal diameter of the internal space 111 of the cartridge 101. During the assembly of the device, the monomer receptacle 102 is plugged into the cartridge 101 from the front and is screwed, by the external thread 109, into the internal thread 108 of the cartridge 101. The plunger 112 of the monomer receptacle 102 seals the internal space 111 of the cartridge 101 in the direction of the rear side (on the top in FIGS. 11 and 12).

An opening facility 118 is provided on the rear side of the monomer receptacle 102 and can be used to push the ampoule 5 in the direction of the plunger 112 in order to open the ampoule 5 and to open the monomer liquid 3 on the inside of the chamber 110. For this purpose, the opening facility 118 comprises a hollow cylinder 120 that is shaped in the form of a sleeve. In this context, the hollow cylinder 120 touches against the internal wall of the chamber 110 and covers it in the area of the rear side of the chamber 110. A closed wall 121 is provided in the hollow cylinder 120 such as to be vertical with respect to the axis of the cylinder geometry of the hollow cylinder 120 such that the hollow cylinder 120 with the closed wall 121 closes the chamber 110, on its rear side, with respect to the outside. The hollow cylinder 120 is attached to a screw-type closure cap 122. The lateral cylinder wall (the cylinder jacket surface) of the hollow cylinder 120 has radial boreholes 123 provided in it that are flush with the gas supply openings 107 in the starting state and storage state of the device (see FIG. 11). By this configuration, the chamber 110 and thereby, through the channels 114, the internal space 111 of the cartridge 101 as well, and thereby the cement powder 4 are connected in a gas-permeable manner to the surroundings of the device in this state. The closure cap 122 comprises an internal thread 124 that fits the external thread 109 of the monomer receptacle 102.

The closure cap 122, or the opening facility 118 as it may be, is screwed part way, but not all the way to a limit stop, onto the rear side of the monomer receptacle 102 and is thus attached to same. It is important that the closure cap 122 can be screwed further onto the monomer receptacle 102 and that the hollow cylinder 120 can thus be inserted more deeply into the chamber 110.

A through-going borehole, into which a securing element 126 in the form of a pin is plugged and is secured from falling out by a holder cap 127, is provided on the rear side of the monomer receptacle 102 and behind the closed wall 121 of the hollow cylinder 120. The securing element 126 prevents the closure cap 122 from being screwed in or out inadvertently and thus prevents the opening facility 118 from being operated inadvertently. The securing element 126 can be released right before a use of the device by pulling off the holder cap 127 and pulling out the pin. The opening facility 118 can then be screwed into the chamber 110.

When the opening facility 118 is screwed in, the boreholes 123 are rotated away from the gas supply openings 107 and are shifted in the longitudinal direction and are closed by the external wall of the hollow cylinder 120. This action closes the device with respect to the outside such that the monomer liquid 3 exiting into the chamber 110 cannot exit from the chamber 110 through the gas supply openings 107.

In order to prevent the closure cap 122 from rotating in the wrong direction and thus to prevent the chamber 110 from being opened on its rear side, a reverse motion lock is provided (not shown in FIGS. 11 and 12). The reverse motion lock prevents the closure cap 122 from being released and/or the opening facility 118 from being released from the monomer receptacle 102. The reverse motion lock can be implemented, for example, as a screw lock in the form of a locking disk or by a pair of wedge lock disks or similar mechanisms. The reverse motion lock not only prevents the opening facility from being released, but the reverse motion lock, if designed appropriately, can prevent the gas supply openings 107 from possibly being opened again by the opening facility 118 being screwed back.

In order to be able to conveniently rotate the opening facility 118 by hand, the rear side end thereof is provided with a handle 128. In order to be able to close the gas supply opening 107 in a gas-tight and pressure-tight manner and to seal the hollow cylinder 120 with respect to the internal wall of the chamber 110, two circumferential seals 130 made of rubber are arranged in circumferential grooves on the external circumference of the hollow cylinder 120. The radial boreholes 123 are arranged between the seals 130, which are situated at a distance from each other in the longitudinal direction. The rear-side seal of the two seals 130 is arranged close to the boreholes 123 such that the gas supply openings 107 are closed rapidly during an axial motion of the hollow cylinder 120 in the longitudinal direction. Alternatively, sealing rings can just as well be arranged about the gas supply openings 107 on the internal wall of the monomer receptacle 102 or about the boreholes 123 on the external wall of the hollow cylinder 120. The gas supply openings 107 are sealed by the rear seal (on the top in FIGS. 11 and 12), when the hollow cylinder 120 is pushed in the direction of the plunger 112.

Likewise, the external circumference of the plunger 112 has two grooves arranged on it, in which two circumferential seals 132 made of rubber are situated and which are situated at a distance from each other in the longitudinal direction. The seals 132 seal the plunger 112 with respect to the internal space 111 of the cartridge 101 and close the rear side of the internal space 111 of the cartridge 101.

The channels 114 and the ring-shaped pore filter 116 are arranged about a mandrel or cutting edge 134 for fracturing the ampoule 5. For this purpose, the mandrel or cutting edge 134 points into the inside of the chamber 110. For this purpose, the ampoule 5 can be pushed onto the mandrel or cutting edge 134 by the hollow cylinder 120 until the bottom of the ampoule 5 fractures. For this purpose, the hollow cylinder 120 has approximately the same diameter as the ampoule body of the ampoule 5. An ampoule head of the ampoule 5 is arranged on the inside of the hollow cylinder 120 in this context. What this attains is that the ampoule 5 is not fractured in the area of the hollow cylinder 120, since the cylindrical ampoule body is very stable, whereas the mandrel or cutting edge 134 can be pushed relatively easily into the bottom of the ampoule 5.

To make sure that the ampoule 5 is not opened during the transport of the device, a spring 136 is arranged about the mandrel or cutting edge 134 in the chamber 110 and positions the ampoule 5 at a distance from the mandrel or cutting edge 134. As an alternative to the spring 136, an elastic compressible closed-pore foam or a compressible hollow rubber body can be arranged about the mandrel or cutting edge 134. When the opening facility 118 is screwed inwards, the spring 136 or the foam is compressed by the ampoule 5 and the bottom of the ampoule 5 is fractured on the mandrel or cutting edge 134.

The front side of the cartridge 101 is closed by a cartridge lid 138. A socket 139 bordering the dispensing opening on the front side is formed in the middle of the cartridge lid 138. The stopper 106 closing the dispensing opening is attached to the socket 139 such that it can be released. The cartridge lid 138 is screwed onto an external thread 142 on the front side of the cartridge 101 by an internal thread 140. The cartridge lid 138 is additionally sealed with respect to the cartridge 101 by a circumferential seal 144.

The internal space 111 of the cartridge 101 contains a loose bead 145 made of zirconium dioxide ceramics as a mixing element. The bead 145 allows the content of the internal space 111 of the cartridge 101 to be mixed by shaking the device. Since the bead 145 has a higher density than the bone cement dough 149, it can be moved in the bone cement dough 149 and even significantly better in a bone cement dough-gas mixture by shaking the device against the bone cement dough 149 and/or the bone cement dough-gas mixture. In this context, the bead 145 flies about in the internal space 111 of the cartridge 101 and mixes the starting components 3, 4 in the process.

The front side of the internal space 111 of the cartridge 101 has a deformable receiving element 150 in the form of a hollow rubber body or a closed-pore foam situated on it, into which the bead 145 can be pressed. A plastic body in the form of a wheel with spokes 151 between which the bead 145 can be accommodated is provided in the receiving element 150. At the "wheel hub," the plastic body forms a sleeve from which the bead 145 slides away. For this purpose, the sleeve of the plastic body can have an asymmetrical design.

The front side of the plunger 112 and the rear side formed by the receiving element 150, which border the front sides of the internal space 111 of the cartridge 101, comprise flanks that rise toward the side wall of the internal space 111 of the cartridge 101 and have a radius of curvature that is larger than the radius of the bead 145. By this configuration, the bead 145 can reach any area of the internal space 111 when the device is shaken. This prevents edges from being present in the internal space 111, in which the cement powder 4 cannot be reached by the bead 145 and thus cannot be mixed into the bone cement dough 149.

A second securing element in the form of a brace 147 can be arranged on the transition from the monomer receptacle 102 into the cartridge 101. The brace 147 can be used to prevent the monomer receptacle 102 from being screwed into the cartridge 101. The brace 147 is pulled off before the monomer receptacle 102 is screwed into the cartridge 101. The brace 147 is not particularly significant and can be omitted just as well.

The work-flow of a method according to the invention is illustrated in the following. Initially, the device is in the starting state (see FIG. 11). In this state, the device has been packaged and sterilized with ethylene oxide. The ethylene oxide can enter into the chamber 110 through the gas supply openings 107 and the boreholes 123, and can enter into the internal space 111 of the cartridge 101 through the pore filter 116, the splinter protector 117, and the channels 114. The gas exchange takes place in a vacuum chamber or in a negative pressure chamber in this context. In this state (see FIG. 11), the device is being unpacked.

In the third embodiment of the device according to the invention, the monomer receptacle 102 does not need to be screwed into the cartridge 101 initially, since the device is already in the maximally screwed-in state (see FIG. 11). From here, the method proceeds mostly analogous to the methods described with regard to the first exemplary embodiment according to FIGS. 1 to 8 and with regard to the second exemplary embodiment according to FIGS. 9 and 10.

In a next step, the securing element 126 is removed and the opening facility 118 is screwed into the chamber 110. It is preferred to hold the device with the cartridge lid 138 downwards in this context. The hollow cylinder pushes the shoulders of the ampoule 5 against the force of the spring 136 in the direction of the mandrel or cutting edge 134 in this context. The gas supply openings 107 are closed by the screw motion of the hollow cylinder 120. Subsequently, the bottom of the ampoule 5 is pushed onto the mandrel or cutting edge 134 and the ampoule 5 fractures on its bottom.

The monomer liquid 3 exits on the bottom of the ampoule 5 in the area of the passage formed by the channels 114. Since the device is being held with the cartridge lid 138 downwards, the monomer liquid 3 driven by gravity immediately flows downwards through the splinter protector 117, the channels 114, and the pore filter 116 into the internal space 111 of the cartridge 101 and distributes in the cement powder 4. Splinters of the ampoule 5, if any, are retained by the splinter protector 117. In order to accelerate the monomer transfer, the monomer receptacle 102 is unscrewed from the cartridge 101. The securing brace 147 is removed first for this purpose. Since the gas supply openings 107 are closed in a gas-tight and pressure-tight manner and the internal space 111 of the cartridge 101 is sealed with respect to the plunger 112 and is closed with respect to the outside, the increase of the volume of the internal space 111 of the cartridge 101 generates a negative pressure in the internal space 111 of the cartridge 101 by which the monomer liquid 3 is aspirated into the internal space 111 of the cartridge 101. As before, the device is being held with the cartridge lid 138 downwards. Moreover, the increase of the internal space 111 of the cartridge 101 also reduces the gas pressure on the inside of the device. The gas at negative pressure is ultimately also present in the internal space 111 of the cartridge 101, over the starting components 3, 4. In this context, the volume of the supernatant gas is at least twice the volume of the monomer liquid 3.

The content of the internal space 111 of the cartridge 101, namely the monomer liquid 3 and the cement powder 4, can be mixed by shaking the device in this state. In the process, the bead 145 flies about in the internal space 111 of the cartridge 101 and thus supports the mixing of the components, whereby all areas are reached due to the bordering of the internal space 111 of the cartridge 101 having a rounded shape such that complete mixing is attained. The internal space 111 of the cartridge 101 then contains the bone cement dough-gas mixture. The bone cement dough 149 is mixed well after repeated shaking.

The device is then reversed such that the cartridge lid 138 faces upwards. The stopper 106 is removed from the dispensing opening. Now, as an option, a hose with a trocar (not shown) can be attached to the socket 139 through which the bone cement dough 149 can be applied under X-ray control in places that are difficult to access. Since the bone cement dough 149 for use in spondylodesis is rather inviscid, the gas bubbles rise. The monomer receptacle 102 is screwed into the cartridge 101 again and the gas escapes in an upward direction out of the dispensing opening. Lastly, the bone cement dough 149 exits through the dispensing opening and/or through the socket 139 from the internal space 111 of the cartridge 101.

Screwing the monomer receptacle 102 further into the cartridge 101, the plunger 112 extrudes the bone cement dough 149 from the device. Lastly, the plunger 112 pushes the bead 145 into the receiving element 150, between the spokes 151, against the cartridge lid 138. The spokes 151 may become deformed in this context. This completes the extrusion process. This state is shown in FIG. 12.

Basically all parts of the three embodiments of the device described through FIGS. 1 to 12 (with the exception of the starting components 3, 4) can preferably consist of plastic and can be produced inexpensively by injection molding. The ampoule 5 preferably consists of glass.

The features of the invention disclosed in the preceding description and in the claims, figures, and exemplary embodiments, can be essential for the implementation of the various embodiments of the invention both alone and in any combination.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. It is expressly intended, for example, that the steps of the methods of using the various devices disclosed above are not restricted to any particular order.

What is claimed:

1. A device for the production of a mixed bone cement dough from a monomer liquid and a cement powder as starting components of the bone cement dough, and for dispensing of the bone cement dough, the device comprising:
    a removable closure;
    a cartridge having a side wall defining a cylindrical internal space in which the cement powder is arranged, a closed front side, a rear side, a thread on the rear side, and a dispensing opening located on the closed front side and closed by the removable closure;
    a monomer receptacle forming a chamber on its inside and having (a) a front side, (b) a wall, (c) a counter-thread that fits with and is screwed to the thread on the rear side of the cartridge to move the monomer receptacle in a longitudinal direction with respect to the cartridge, (d) a cylindrical plunger having a side facing into the chamber, being located on the front side, and defining a passage that is permeable to gases and the monomer liquid but impermeable to the cement powder and that connects the internal space of the cartridge to the chamber of the monomer receptacle, the plunger tightly closing the internal space of the cartridge on its rear side except for the passage, and (e) at least one gas supply opening connecting the chamber to the surroundings of the device and being located in the wall of the monomer receptacle;
    a monomer liquid container containing the monomer liquid and being located in the chamber of the monomer receptacle; and
    an opening facility for opening the monomer liquid container within the chamber of the monomer receptacle, the opening facility closing the at least one gas supply opening before the monomer liquid container is opened, wherein the opening facility has a reverse motion lock that prevents the at least one gas supply opening from being opened again after the at least one gas supply opening has been closed, the reverse motion lock including a thread that connects the reverse motion lock to the monomer receptacle and the at least one gas supply opening is closed when the opening facility is screwed into the chamber.

2. The device according to claim 1 further comprising a first releasable securing element preventing the opening facility from being operated or a second releasable securing element preventing the monomer receptacle from being screwed into the cartridge or both the first releasable securing element and the second releasable securing element.

3. The device according to claim 1 further comprising a compressible supporting element arranged between the plunger and the monomer liquid container and a mandrel or a cutting edge arranged on the side of the plunger facing into the chamber of the monomer receptacle for fracturing the monomer liquid container, whereby the compressible supporting element keeps the monomer liquid container at a distance from the mandrel or cutting edge.

4. The device according to claim 1 further comprising at least one loose mixing element arranged in the internal space of the cartridge such as to be freely mobile.

5. The device according to claim 4 further comprising at least one protrusion arranged on the closed front side of the cartridge, the at least one protrusion being located adjacent to the dispensing opening and extending into the internal space of the cartridge.

6. The device according to claim 4 further comprising a deformable annular disk having a front side arranged in the internal space of the cartridge and a height that increases in a radial direction outward towards the side wall defining the internal space.

7. The device according to claim 4 wherein the at least one loose mixing element has a higher density than polymethylmethacrylate and consists of a corundum, of $\alpha$-corundum, of a zirconium oxide, of tetragonal $ZrO_2$, or of $ZrO_2$ that is cubic-stabilized with $Y_2O_3$.

8. The device according to claim 4 wherein the internal space of the cartridge is limited by at least one of a rounded front base surface having a radius of curvature or a rounded rear base surface having a radius of curvature.

9. The device according to claim 8 wherein the at least one mixing element is a bead having a radius that is equal to or smaller than the radius of curvature of the front base surface or of the rear base surface limiting the internal space of the cartridge.

10. The device according to claim 1 wherein the monomer liquid container is an ampoule made of glass or plastic having an ampoule body with a cylindrical wall, the opening facility comprises a hollow cylinder that is mobile in the monomer receptacle in a longitudinal direction of the chamber of the monomer receptacle, and the hollow cylinder is flush with the cylindrical wall of the ampoule such that the ampoule can be pushed in a direction toward the internal space of the cartridge by the hollow cylinder.

11. The device according to claim 1 further comprising a mandrel and wherein the opening facility has a thread that engages the counter-thread of the monomer receptacle such that the opening facility screws into the chamber of the monomer receptacle and pushes the monomer liquid container toward the mandrel which fractures, cuts, or punctures the monomer liquid container.

12. The device according to claim 1 wherein the thread on the rear side of the cartridge is an internal thread and the counter-thread of the monomer receptacle is an external thread.

13. The device according to claim 12 wherein the plunger has a diameter larger than the internal thread on the rear side of the cartridge.

14. The device according to claim 1 wherein the front side of the cartridge has an external thread and the cartridge has a cartridge lid screwed onto the external thread to close the front side of the cartridge and in which the dispensing opening is arranged, the cartridge lid connected to the side wall of the cartridge in a gas-tight and liquid-tight manner.

15. The device according to claim 1 further comprising a first limit stop, wherein the monomer receptacle has a rear side, the opening facility has a closure cap that screws onto the rear side of the monomer receptacle and closes the chamber in a gas-tight manner, and the first limit stop prevents the closure cap from being screwed further onto the monomer receptacle.

16. The device according to claim 15 further comprising a sleeve arranged on the closure cap that can be plugged or screwed into the chamber such that the closure cap closes the chamber in a gas-tight manner.

17. The device according to claim 1 further comprising a second limit stop, wherein when the monomer receptacle is maximally unscrewed from the cartridge up to the second limit stop, the internal space of the cartridge has a free volume at least equal to the volume of the monomer liquid in the monomer liquid container.

18. A device for the production of a mixed bone cement dough from a monomer liquid and a cement powder as starting components of the bone cement dough, and for dispensing of the bone cement dough, the device comprising:
a removable closure;
a cartridge having a side wall defining a cylindrical internal space in which the cement powder is arranged, a closed front side, a rear side, a thread on the rear side, and a dispensing opening located on the closed front side and closed by the removable closure;
a monomer receptacle forming a chamber on its inside and having (a) a front side, (b) a wall, (c) a counter-thread that fits with and is screwed to the thread on the rear side of the cartridge to move the monomer receptacle in a longitudinal direction with respect to the cartridge, (d) a cylindrical plunger having a side facing into the chamber, being located on the front side, and defining a passage that is permeable to gases and the monomer liquid but impermeable to the cement powder and that connects the internal space of the cartridge to the chamber of the monomer receptacle, the plunger tightly closing the internal space of the cartridge on its rear side except for the passage, and (e) at least one gas supply opening connecting the chamber to the surroundings of the device and being located in the wall of the monomer receptacle;
an ampoule made of glass or plastic having an ampoule body with a cylindrical wall containing the monomer liquid and being located in the chamber of the monomer receptacle; and
an opening facility for opening the ampoule within the chamber of the monomer receptacle, the opening facility closing the at least one gas supply opening before the ampoule is opened, the opening facility including a hollow cylinder that is mobile in the monomer receptacle in a longitudinal direction of the chamber of the monomer receptacle, and the hollow cylinder is flush with the cylindrical wall of the ampoule such that the ampoule can be pushed in a direction toward the internal space of the cartridge by the hollow cylinder,
wherein the hollow cylinder has a side wall with a borehole and at least one circumferential sealing ring, the at least one gas supply opening merges with the borehole into the chamber of the monomer receptacle such that, upon movement of the hollow cylinder into the chamber, the at least one gas supply opening is closed in a liquid-tight or gas-tight manner by the side wall of the hollow cylinder with the at least one circumferential sealing ring traveling over the at least one gas supply opening when the hollow cylinder moves into the chamber and seals the chamber.

* * * * *